US010799649B2

(12) United States Patent
Marlin et al.

(10) Patent No.: US 10,799,649 B2
(45) Date of Patent: Oct. 13, 2020

(54) SENSOR SYSTEMS FOR DRUG DELIVERY DEVICES

(71) Applicant: UNL Holdings LLC, New York, NY (US)

(72) Inventors: Arthur Marlin, Willow Grove, PA (US); William King, Jeffersonville, PA (US); Lee Cross, Chesterbrook, PA (US); Madeline Davis, Malvern, PA (US); Andrew King, Malvern, PA (US)

(73) Assignee: UNL Holdings LLC, New York, NY (US)

( * ) Notice: Subject to any disclaimer, the term of this patent is extended or adjusted under 35 U.S.C. 154(b) by 420 days.

(21) Appl. No.: 15/507,510

(22) PCT Filed: Aug. 28, 2015

(86) PCT No.: PCT/US2015/047503
§ 371 (c)(1),
(2) Date: Feb. 28, 2017

(87) PCT Pub. No.: WO2016/033507
PCT Pub. Date: Mar. 3, 2016

(65) Prior Publication Data
US 2018/0236181 A1 Aug. 23, 2018

Related U.S. Application Data

(60) Provisional application No. 62/043,217, filed on Aug. 28, 2014, provisional application No. 62/043,239, (Continued)

(51) Int. Cl.
*A61M 5/44* (2006.01)
*A61M 5/20* (2006.01)
(Continued)

(52) U.S. Cl.
CPC .............. *A61M 5/445* (2013.01); *A61B 90/98* (2016.02); *A61M 5/20* (2013.01); *A61M 5/44* (2013.01);
(Continued)

(58) Field of Classification Search
CPC .......... A61M 5/445; A61M 5/20; A61M 5/44; A61M 2005/31588; A61M 2205/36; A61B 90/98
See application file for complete search history.

(56) References Cited

U.S. PATENT DOCUMENTS 8,105,277 B2 1/2012 Gröber et al.
2004/0247016 A1* 12/2004 Faries, Jr. ............. A61J 1/1487
374/162
(Continued)

FOREIGN PATENT DOCUMENTS

CN 2170111 6/1994
WO WO 2006/108026 A2 10/2006
(Continued)

OTHER PUBLICATIONS

International Preliminary Report on Patentability for International Application No. PCT/US2015/047503, entitled: "Sensor Systems for Drug Delivery Devices," dated Mar. 8, 2016.
(Continued)

*Primary Examiner* — Theodore J Stigell
(74) *Attorney, Agent, or Firm* — Hamilton, Brook, Smith & Reynolds, P.C.

(57) ABSTRACT

Systems for drug delivery devices include a temperature control system and an identification system. A temperature control system configured to sense and control temperature of a cartridge containing a drug includes a heater, one or more temperature sensors, and a control unit. An identification system configured to identify a cartridge containing a drug includes a control unit and a tag sensor that is electrically coupled to the control unit, wherein the tag sensor is activated upon detecting a presence of the cartridge. A drug delivery device includes both the temperature control system and the identification system such that the control unit of the device may process the information of the drug that is
(Continued)

received from the tag sensor of the identification system, and based on at least a portion of the processed information, determine and control the temperature of the drug within a cartridge.

21 Claims, 12 Drawing Sheets

Related U.S. Application Data filed on Aug. 28, 2014, provisional application No. 62/080,603, filed on Nov. 17, 2014.

(51) Int. Cl.
*A61B 90/98* (2016.01)
*A61M 5/315* (2006.01)

(52) U.S. Cl.
CPC ............ *A61M 2005/31588* (2013.01); *A61M 2205/18* (2013.01); *A61M 2205/3368* (2013.01); *A61M 2205/36* (2013.01); *A61M 2205/60* (2013.01); *A61M 2205/6027* (2013.01); *A61M 2205/6054* (2013.01)

(56) References Cited

U.S. PATENT DOCUMENTS

| | | | | |
|---|---|---|---|---|
| 2007/0268340 A1* | 11/2007 | Dacquay | ............... | A61F 9/0017 347/68 |
| 2007/0270748 A1* | 11/2007 | Dacquay | ............... | A61F 9/0017 604/131 |
| 2007/0270760 A1* | 11/2007 | Dacquay | ............... | A61F 9/0017 604/208 |
| 2007/0270777 A1* | 11/2007 | Dacquay | ............... | A61F 9/0017 604/521 |
| 2008/0306443 A1* | 12/2008 | Neer | ..................... | A61M 5/007 604/121 |
| 2009/0227979 A1* | 9/2009 | Sanchez, Jr. | ............ | A61M 5/20 604/506 |
| 2010/0057003 A1* | 3/2010 | Dos Santos | ........... | A61F 9/0017 604/114 |
| 2012/0130207 A1 | 5/2012 | O'dea et al. | | |

FOREIGN PATENT DOCUMENTS

| | | |
|---|---|---|
| WO | WO 2006/122167 A2 | 11/2006 |
| WO | WO 2007/088444 A1 | 8/2007 |
| WO | 2008105955 A2 | 9/2008 |
| WO | WO 2008/105958 A2 | 9/2008 |
| WO | WO 2012/022771 A2 | 2/2012 |
| WO | WO 2012/145685 A1 | 10/2012 |
| WO | WO 2014/066256 A1 | 5/2014 |

OTHER PUBLICATIONS

European Patent Office, International Search Report in International Patent Application No. PCT/US2015/047503, dated Mar. 8, 2016, 8 pp.

European Patent Office, Written Opinion in International Patent Application No. PCT/US2015/047503, dated Mar. 8, 2016, 8 pp.

\* cited by examiner

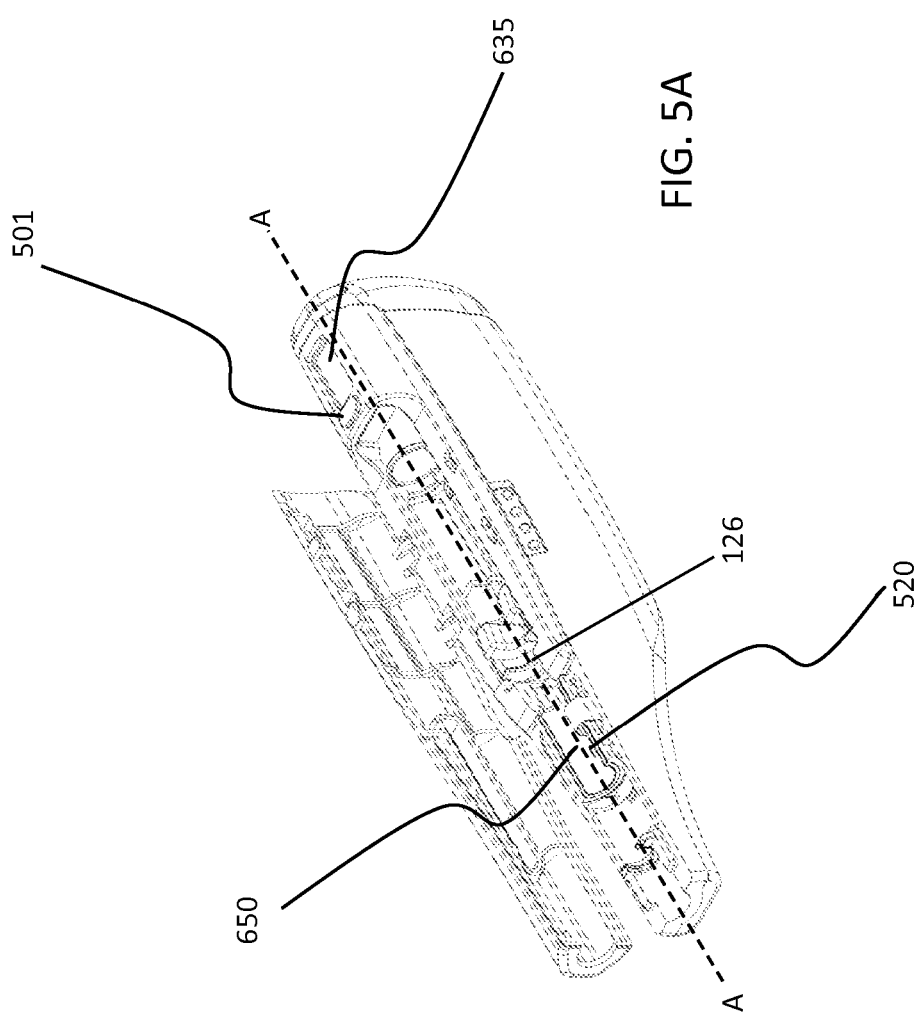

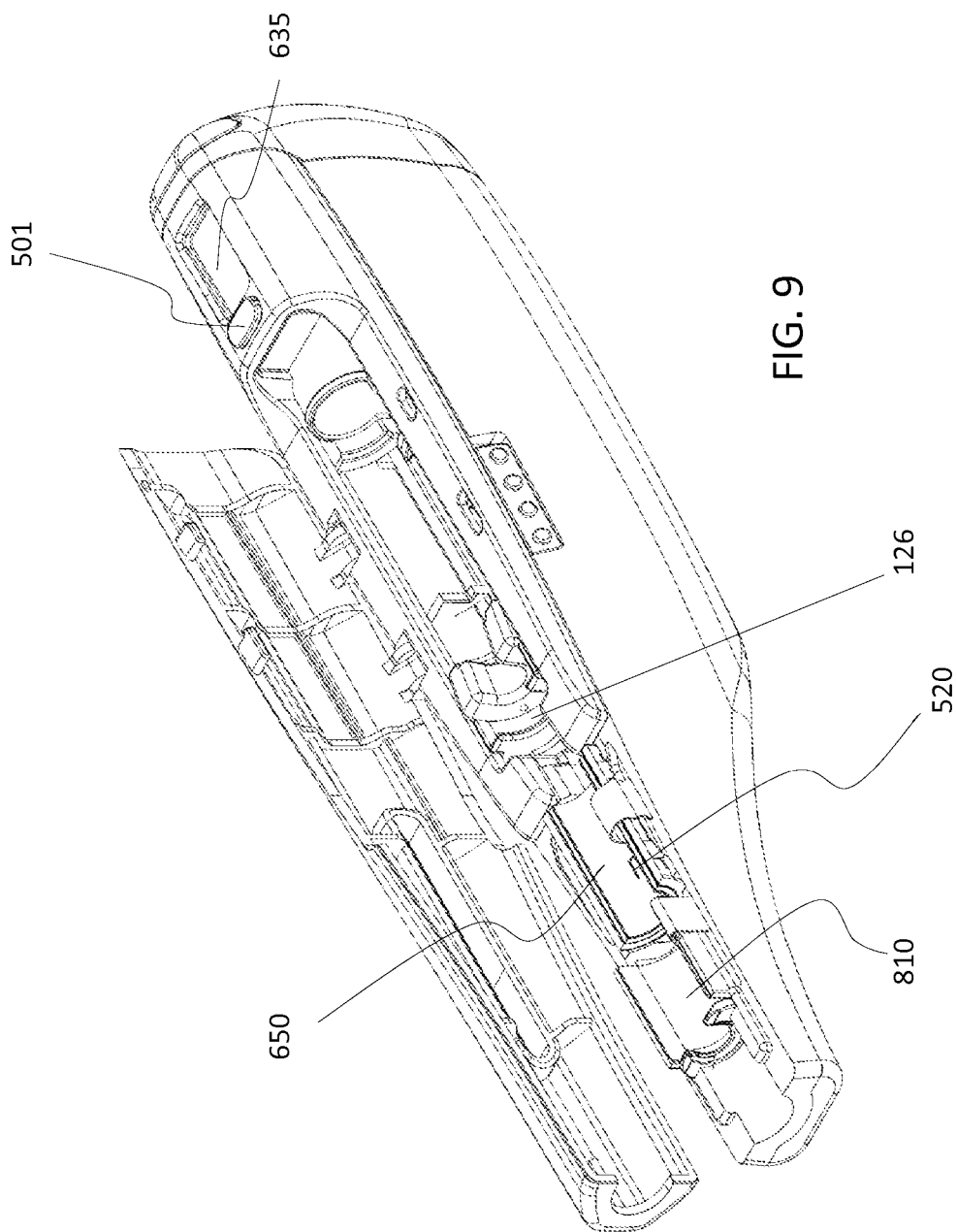

SENSOR SYSTEMS FOR DRUG DELIVERY DEVICES

CROSS-REFERENCE TO RELATED APPLICATIONS

This patent application is a national phase application of International Patent Application No. PCT/US2015/047503, filed Aug. 28, 2015, which claims priority to U.S. Provisional Patent Application No. 62/080,603 filed Nov. 17, 2014; No. 62/043,217 filed Aug. 28, 2014; and No. 62/043,239 filed Aug. 28, 2014; each of which is incorporated herein by reference in its entirety for alb purposes.

FIELD OF THE INVENTION

The present invention relates to sensor systems. More specifically, the embodiments of the present invention relate to temperature sensing and control systems, and identification systems, for drug delivery devices. The present invention also relates to drug delivery devices incorporating such sensor systems, and their methods of operation or use.

BACKGROUND OF THE INVENTION

Manually activated pre-filled cartridges are commercially available from a variety of manufacturers, including the owner and assignee of the present invention. The owner and assignee of the present invention has developed a syringe which offers a unique and elegant integrated mechanism for retraction of the needle and/or syringe. Currently, visual, tactile or audible indicators are generally linked to the end of stroke or some other mechanical mechanism and not to the end of dose. The integrated needle retraction syringe retracts the needle into the barrel, removing it from the patient's skin, once the dose is complete.

Pre-filled cartridges are used in the administration of drug solutions, drug suspensions, vaccines, medicinal therapies, and any other liquid medicament by parenteral injection. Such pre-filled cartridges include a primary drug chamber, a hypodermic needle permanently affixed to and in fluid communication with the drug chamber, and a piston slidably received in the drug chamber. The pistons of the pre-filled cartridges often include a plunger sub-assembly, which may include a plunger inner and a plunger outer, to force the liquid medicament from the needle. Pre-filled cartridges are typically prepared by pharmaceutical companies or sterile filling contractors in a sterile filling room in which the drug and the cartridge are brought together in a sterile manufacturing environment wherein all components and drug solutions are isolated from microbial contamination.

In contrast to manually activated pre-filled cartridges, automatic injection devices commonly known as "auto injectors" or "wearable injectors" are also available. Such automatic injection devices, once triggered by the user, use an automatic mechanism to insert a fluid conduit, such as a hypodermic needle or cannula, into the recipient's flesh at the injection site and force the liquid medicament out of a medicine compartment, through the fluid conduit, and into the recipient. In addition, some auto injectors also incorporate retraction mechanisms to automatically retract the needle after use. Auto injectors have proven particularly useful in allowing the medically untrained user to administer a parenteral injection, and can provide both psychological and physical advantages to patients.

Patients needing to inject medication for chronic disease management have used auto injectors since the first auto-injector was introduced in the 1990s. An auto-injector provides protection for the primary container, generally a pre-filled syringe, primary container, or cartridge, and offers an easy way for automatic injection of medication. These devices offer increased convenience and autonomy for patients as well as providing a competitive advantage to the pharmaceutical partner through device differentiation and increased sales through compliance of the patient to their therapy. Auto injectors may also be beneficial in delivering large volumes and viscous drugs. Auto injectors also work to prevent needle stick injuries by housing the needle within a chamber, inserting the needle into the patient for drug introduction, then retracting the needle back into the housing utilizing, for example, reverse drive mechanisms.

Some auto injectors have been designed to accept commercially available, manually activated pre-filled cartridges. Such configurations may be made in the form of cartridges for auto injectors (e.g., reusable auto injectors) or single-use auto injectors. The syringes developed and manufactured by the owner and assignee of the present invention offer unique and elegant integrated refraction mechanism for needle safety. A number of different syringes and cartridge configurations may be utilized in such auto injectors, including those sold by the assignee and owner of the present invention under the trade names "Unifill" and "Unifill Finesse" and covered by one or more of the following: U.S. Pat. Nos. 6,083,199; 7,500,967; 7,935,087; 8,021,333; 8,002,745; 8,052,654; 8,114,050; 8,167,937; 8,361,035; 8,945,048; 8,702,653; and 8,979,795; U.S. Patent Pub. No. 2011/0015572 and U.S. Patent Pub. No. 2013/0226084; and International PCT App. Nos. PCT/AU2010/001505, PCT/AU2010/001677; PCT/AU2011/000515; PCT/US2012/067793; PCT/US2014/050066; and PCT/US2014/024781; all of which are incorporated herein by reference, in their entirety, for all purposes. Such syringes are provided herein as merely examples of syringes capable of being utilized as cartridges within the auto injectors of the present invention, and the embodiments of the present invention are readily configurable to adapt or accept a broad range of syringes for drug delivery to a patient. The automatic injectors are also designed to accept a variety of syringes as filled drug-container cartridges, i.e., as pre-filled syringes, including the "Unifill" and "Unifill Finesse" syringes described herein.

Moreover, it would be beneficial if the drug products are administered at their admissible temperature via the auto injectors. This is because some drugs disintegrate or decompose, thus losing their efficacy, when exposed above or below their operating temperature range.

Typically, drug products are refrigerated to increase their shelf-life, and prior to being administered to a patient. However, if the temperature of the drug does not readily rise to the appropriate target temperature upon being exposed to the ambient environment and during the administration of the drug, the efficacy of the drug may be substantially lost and may potentially be harmful to the patient.

Additionally, temperature variation of the drug may also give rise to issues associated with the viscosity of the drug. For example, some medicinal products exhibit higher viscosity when the temperature is lower than the operating temperature of the drug. This may present difficulty for the patient to self-administer the drug. The automatic injector device may also fail to deliver a complete dose due to the higher viscosity of the drug.

Furthermore, the patient may be unaware of the ineffectiveness or even harmfulness of the drug due to the decomposition or due to changes in the viscosity of the drug that had stemmed from the temperature variation (e.g., the decomposition may not be visible to the naked eye of the patient). As a result, any administration of such drug products may lead to erroneous treatment, and consequently be severely detrimental to the health of the patient.

Therefore, there is a need for improved automatic injector devices that operate consistently within an operating temperature range of the drug products, and particularly, that accepts variety of drug cartridges that can be temperature controlled. These improved auto injectors may potentially overcome the challenges associated with administering drug products via auto injectors at their admissible temperatures.

The inventions of the present invention are described with relation to a limited example of embodiments, however, the inventions may be used with a number of different automatic injectors, including those developed by the assignee and owner of the present invention which are covered by one or more of the following: International PCT App. Nos. PCT/US2012/53174, PCT/US2012/53241, PCT/US2012/054861, PCT/US2013/057367, PCT/US2013/030624, PCT/US2014/013019, PCT/US2013/050075, PCT/US2013/057327, PCT/US2013/030478, PCT/US2014/013005, PCT/US2012/052129, PCT/US2014/034974, PCT/US2013/049314, and U.S. Pat. No. 8,808,244 all of which are incorporated herein by reference, in their entirety, for all purposes.

BRIEF SUMMARY OF THE INVENTION

The present invention relates to novel automatic injectors for drug delivery which incorporate temperature sensors and/or temperature control elements. The development of devices that increasingly allow patients to self-administer drugs in the home has the potential to reduce health care costs, reduce patient stress and inconvenience, and reduce demand on physicians, nurses, and other care takers. However, patient compliance with prescribed at-home treatments may potentially decrease the effectiveness of at-home treatment. The incorporation of identification systems allows for the identification and communication of: the type of syringe and/or cartridge used for delivery, manufacturing ID, the lot and/or serial number of the syringe and/or cartridge, type of drug delivered, serial and/or lot number of drug delivered, expiration date of drug delivered, amount of drug to be delivered, rate of drug delivery, temperature of drug at time of delivery, and other operational parameters necessary for the accurate delivery of the drug medicament by the automatic injector. This information may then be stored in memory; the memory may be stored within the automatic injector or may be remotely located. By recognizing, communicating, and/or receiving this information, the automatic injector may set the operational parameters necessary for drug delivery, and inform or alert the user of errors or desired operational conditions. This data may then be viewed by a patient's physician, nurse, or other care giver who would then be able to determine the patient's level of compliance. This information could additionally be used when determining the effectiveness of drugs by allowing patient compliance to be accounted for. The automatic injectors of the present invention which include such identification systems help to reduce the burden on the patient. In some cases, drug efficacy or shelf life may be affected by the temperature at which the drug is stored. Additionally, some drugs may have specific temperature ranges at which they should be administered in order to optimize efficacy or to reduce pain to the patient. Administering a drug which is of a low temperature may be painful to a patient due to the difference between the temperature of the drug and the temperature of the patient's body. However, these requirements increase the demands on and requirements of the self-administering patient. Not only do they need to ensure that they are administering the drug at the prescribed intervals they must also ensure that the drug is within the specified temperature. These requirements may lead to decreased compliance with the prescribed treatment. The novel automatic injectors of the present invention which include temperature sensors and/or temperature controlling elements similarly help to reduce the burden on the patient.

In some embodiments, the present invention provides, a temperature control system for a drug delivery device configured to sense and control temperature of a cartridge containing a drug. The temperature control system may include a heater that is configured to be in close proximity to the cartridge and configured to warm the drug; a first temperature sensor that is positioned in close proximity to the heater and configured to detect a first temperature value of the heater; a second temperature sensor that is positioned in close proximity to the cartridge configured to detect a second temperature value of the drug. The temperature control system may include a first control unit that is electrically coupled to the heater, the first temperature sensor and the second temperature sensor. Moreover, the first control unit is configured to determine whether the detected first temperature value of the heater is below a first alarm set point temperature value and the detected second temperature value of the drug is within a range of drug operating temperature values; The first control unit may further adjust the detected second temperature value of the drug to an operational temperature value of the drug that is within the range of drug operating temperature values, based on the determination that the first detected temperature value is below the first alarm set point temperature value and the detected second temperature value is not within the range of drug operating temperature values.

In some embodiments, the first control unit is a feedback control unit that receives the detected first and the second temperature values from the first and the second temperature sensors, respectively.

In some examples, the first control unit may transmit an error signal upon determination that the detected first temperature value of the heater and the detected second temperature value of the drug is above the first alarm set point temperature value or below a second alarm set point temperature value. Moreover, the first alarm set point temperature value and the second alarm set point temperature values are pre-determined values that are programmed in respective storage units of the first and second temperature sensors. Furthermore, the adjustment of the detected second temperature value may include transmission of a command signal, by the first control unit, to the heater to warm the drug within a predetermined time while monitoring the first temperature value of the heater.

In some embodiments, the temperature control system may control the transmitted command signal to warm the drug via the heater within the predetermined time, based on a thermal profile of the drug.

The temperature control system transmit, in another example, an error signal to a display unit that is coupled to the first control unit, upon determining that the second temperature was not adjusted to the operational temperature within the predetermined time.

In some implementations, the temperature control system may prompt a user to activate one or more operations related to drug delivery from the cartridge upon the adjustment of the second detected temperature to the operational temperature. The temperature control system may further store the operational temperature value, after the adjustment of the detected second temperature of the drug, in a storage unit that is coupled to the first control unit. Moreover, the range of the operating temperature values may have an upper limit value and a lower limit value that are programmed to be percentages of the operational temperature value.

In at least one embodiment, the temperature control system may transmit a command signal to the heater upon receiving an activation signal from a user that indicates initiation of warming of the cartridge containing the drug.

In some embodiments, the present invention provides an identification system or an identification sensor system for a drug delivery device configured to identify a cartridge containing a drug. The identification system may include a control unit and a tag sensor that is electrically coupled to the control unit. The identification system may activate the tag sensor, for example, to initiate a contactless communication with the cartridge upon detecting a presence of the cartridge.

In one embodiment, the identification system may include a cartridge sensor that is configured to send a status signal to the control unit that indicates the presence of the cartridge. In another embodiment, the identification system may emit an interrogating signal towards the cartridge to initiate the contactless communication.

In some implementations, the tag sensor may be of an arcuate shape and may substantially arcuately align with a cartridge tag that is affixed to a surface of the cartridge.

Moreover, the contactless communication is a wireless communication and the tag sensor may electromagnetically stimulate the cartridge tag with the interrogating signal upon being substantially aligned with the cartridge tag.

In one example, the identification system may receive a response signal from the cartridge tag when the cartridge tag is stimulated by the interrogating signal. The response signal may include information related to the drug contained in the cartridge.

Yet in another implementation, the identification system may determine whether the cartridge tag is readable based on the information received by the tag sensor. The identification system may further determine an identification of the cartridge when the cartridge tag is readable.

The identification system, in some embodiments, may include a communication unit, and may determine whether the information from the cartridge tag is valid by consulting with a remote computer device via the communication unit. Furthermore, the information may include parameters selected from a group consisting of: an expiration date of the drug, a manufacturing identity (ID), and a drug ID of the drug. In one embodiment, the identification system may determine whether the drug is being recalled based on at least one or a combination of the parameters.

In some implementations, the identification system may configure one or more control parameters related to a drug delivery process upon the reception of the information from the cartridge tag.

In some embodiments, the present invention may provide an automatic injector (AI) device adapted to receive a cartridge containing a drug including a barrel, a needle, and a plunger assembly including a plunger seal, the cartridge defining a longitudinal axis. The AI device may include a housing, a cartridge carrier adapted to receive at least a portion of the cartridge. The cartridge carrier may be disposed for movement relative to the housing in a direction parallel to the longitudinal axis of the cartridge. The AI device may further include a plunger carrier disposed for movement relative to the cartridge carrier, an elongated drive device coupled to the plunger carrier, and the elongated drive device may be disposed to provide movement of the plunger carrier in a direction parallel to the longitudinal axis of the cartridge. The AI device may further include a motor, and a transmission assembly coupling the motor to the elongated drive device. The AI device may further include the temperature control system and the identification system and a second control unit. The AI device may be configured to process the information of the drug that is received from the tag sensor of the identification system, and based on at least a portion of the processed information, may determine whether the detected first temperature value of the heater of the temperature control system, is below a first alarm set point temperature value and the detected second temperature value of the drug is within a range of drug operating temperature values, and further control the motor based on the processed information.

The AI device, in some example, may transmit a command signal to the heater upon receiving an activation signal from the tag sensor that indicates that the tag sensor is activated and has wirelessly received the drug information. Moreover, the adjustment of the detected second temperature further includes transmission of a command signal to the heater to warm the drug within a predetermined time based on the warming period information received from the cartridge tag.

In one example, the AI device may store the operating temperature value after the adjustment of the detected second temperature of the drug, and the retrieved drug information, in a remote storage unit via the communication unit.

In some embodiments, the AI device may further control the cartridge carrier to move the cartridge from a first position where the needle is within the housing, to a second position where the needle extends distally from the housing, based on the information received from at least one of the temperature control sensor and the identification system.

Yet in another example, the second control unit may be the same as the first control unit of the temperature control system and the control unit of the identification system.

In one embodiment, the reusable automatic injector could be adapted for use with any type of retractable or safety syringe, but for simplicity, the invention is described when using a syringe similar to those sold by the owner and assignee of the present invention under the trade name "Unifill." Because the components of the automatic injector and the drive control mechanism are able to repeatedly load, inject, and eject drug cartridges for injection of drug treatments to a patient, they are considered reusable automatic injectors.

In a further embodiment, the AI device may include a sensor carriage that may be configured to receive the tag sensor. The AI device may activate the tag sensor to initiate a contactless communication with the cartridge upon detecting the presence of the cartridge within the sensor carriage.

In another embodiment, the motion of the plunger carrier may be controlled by the control unit based on the information received by the tag sensor from the cartridge tag to control a rate of drug delivery.

The embodiments shown and detailed herein disclose only a few possible variations of the present invention; other similar variations are contemplated and incorporated within the breadth of this disclosure. As would be readily appreciated by an ordinarily skilled artisan, a number of parameters, shapes, and dimensions described above may be modified while remaining within the breadth and scope of the present invention.

BRIEF DESCRIPTION OF THE DRAWING(S)

The following non-limiting embodiments of the invention are described herein with reference to the following drawings, wherein:

FIG. 5A is an isometric view of another embodiment of the automatic injector;

FIG. 9 is an isometric view of another embodiment of the automatic injector containing both a temperature sensing and temperature control element and a data communications element, such as an RFID antenna or sensor.

DETAILED DESCRIPTION OF THE INVENTION

Figure 1:
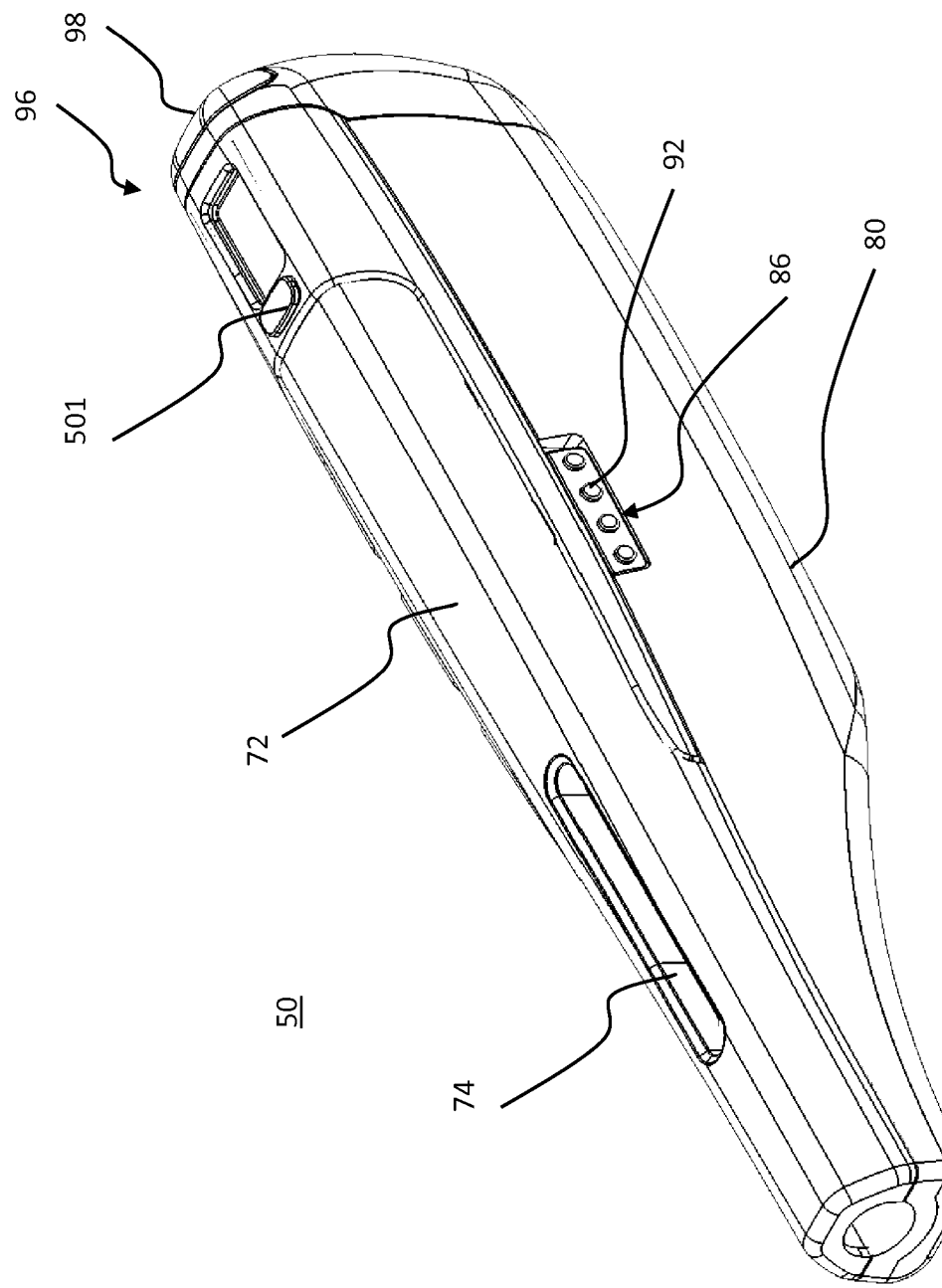
FIG. 1 is an isometric view of an automatic injector of the present disclosure.

The present invention relates to automatic injectors for drug delivery which incorporate temperature sensors and temperature control elements. The development of devices that increasingly allow patients to self-administer drugs in the home has the potential to reduce health care costs, reduce patient stress and inconvenience, and reduce demand on physicians, nurses, and other care takers. In some cases, drug efficacy or patient comfort is improved if the drug is administered when the drug is within a specific temperature range or is near to the same temperature as the patient's body temperature. Further, the temperature of the drug may be related to the drug's viscosity, with some viscosities preferred for drug administration. At the same time, the shelf life of at least some drugs is increased when the drug is stored at a reduced temperature. In order to increase the probability of the drug being administered at the appropriate temperature the automatic injection devices of the present disclosure provide elements that are able to determine if the drug and/or drug container are within a specified range or above a specified temperature. In at least one embodiment, if the automatic injection device determines that the drug or drug container is not within the specified temperature range it will prevent the patient from performing one or more of the steps of: needle shield removal, needle insertion, and drug injection. In further embodiments, the automatic injector further comprises temperature control elements such that the automatic injector may influence the temperature of the drug or drug container until the temperature is within the specified range. The auto injectors of the present invention may be further configured to interpret a cartridge tag/syringe tag located on a cartridge or syringe. The data tag may include information related to the drug contained therein that may serve as an input to the operation of the auto injector. This may be achieved by the incorporation of identification system or an identification sensor system that allows for the identification and communication of: the type of syringe and/or cartridge used for delivery, the lot and/or serial number of the syringe and/or cartridge, type of drug delivered, serial and/or lot number of drug delivered, expiration date of drug delivered, amount of drug to be delivered, rate of drug delivery, temperature of drug at time of delivery, and other operational parameters necessary for the accurate delivery of the drug medicament by the automatic injector.

The automatic injectors of the present invention may be single-use devices or reusable automatic injectors and may additionally be wearable automatic injectors. More specifically, the embodiments of the present invention relate to automatic injection devices which utilize drive mechanisms, injection syringes or drug containers, and perform one or more of the steps of: removal of a safety cap or needle shield, needle insertion, drug dose delivery, and syringe and/or needle retraction. The present invention also relates to automatic injection devices comprising temperature sensors and/or temperature control elements, and their methods of use. Furthermore, optionally, the automatic injector may be configured to adjust the dose volume, such as by expending a portion of the drug dosage to a reservoir, prior to needle injection and drug dose delivery into a user.

As used herein to describe the temperature sensors, temperature control elements, automatic injectors, cartridges, or any of the relative positions of the components of the present invention, the terms "axial" or "axially" refer generally to a longitudinal axis "A" around which reusable automatic injector is preferably positioned although not necessarily symmetrically there-around. The terms "proximal," "rear," "rearward," "back," or "backward" refer generally to an axial direction in the direction of the plunger rod or transmission assembly. The terms "distal," "front," "frontward," "depressed," or "forward" refer generally to an axial direction in the direction of the needle or rigid needle shield. The term "laterally" refers to a direction in a plane normal to a longitudinal axis "A." The term "radial" refers generally to a direction normal to axis A.

As used herein, the term "glass" should be understood to include other similarly non-reactive materials suitable for use in a pharmaceutical grade application that would normally require glass. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" does not include either glass or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration.

"Fluid" refers primarily to liquids, but can also include suspensions of solids dispersed in liquids, and gasses dissolved in or otherwise present together within liquids inside the fluid-containing portions of cartridges. The terms "drug," "medicine," and "medicament" are used to refer to any substance that is administered from a cartridge through a needle or cannula, and is not limited to pharmaceutical substances, but may include, for example, vitamins or minerals.

As used herein, the terms "automatic injector" and "auto-injector" are meant to refer to the same reusable devices, which may also be referred to by the acronym "RAI". The inventions described here are also applicable to wearable injectors, as detailed herein, and the term "automatic injector" is used herein to incorporate the same.

Figure 2:
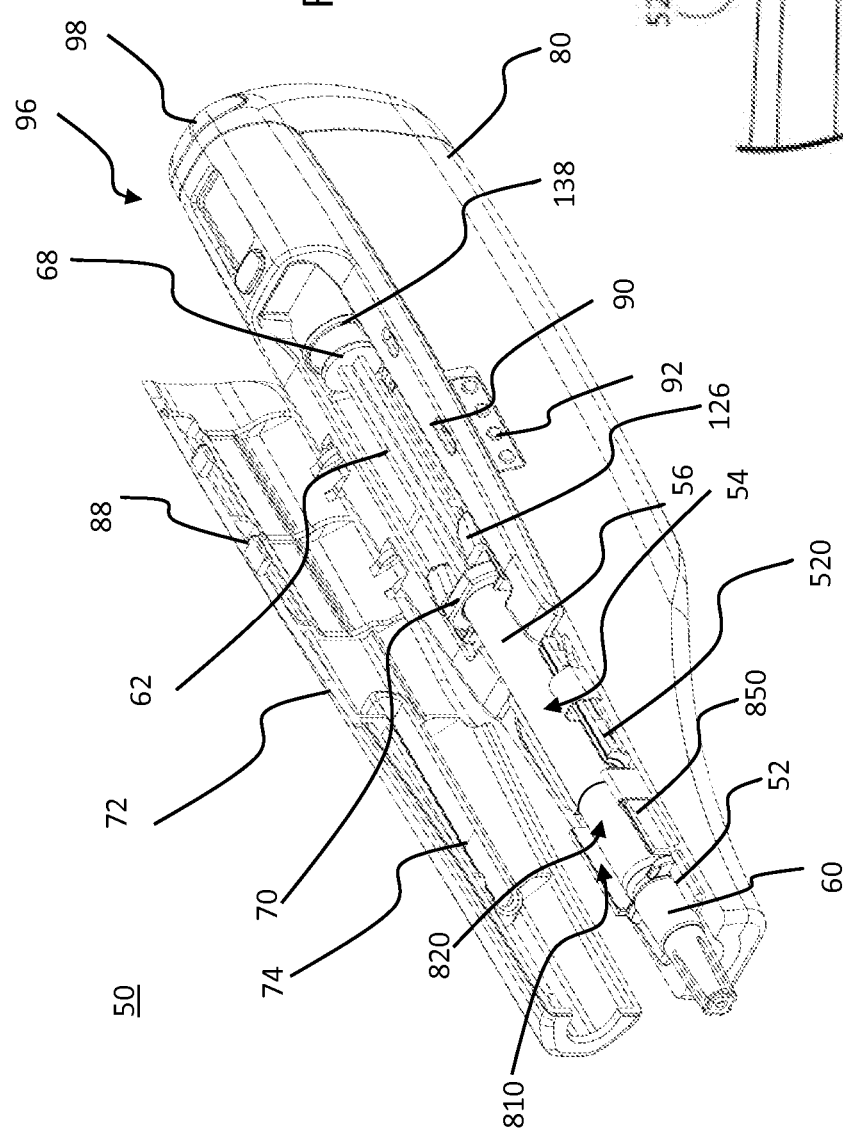
FIG. 2 is an isometric view of an automatic injector of the present disclosure in which a syringe is in place.

Turning first to FIGS. 1 and 2, there is shown an automatic injector 50 according to at least one embodiment of the invention. The automatic injector 50 includes a housing 52 adapted to receive and support a syringe or cartridge 54 for injection, as well as various components of the injection system. A variety of cartridges 54 may be utilized in the reusable automatic injector 50 of the present invention, including those having automatic retraction features. For example, a safety syringe with integrated needle retraction may be used with the reusable automatic injector 50. One example of such a cartridge 54 in the form of a safety syringe is illustrated in FIG. 2, and includes a barrel 56, a needle (not shown), a rigid needle shield 60, and a plunger assembly including a plunger seal 64, a plunger rod 62, and a plunger head 68. In the illustrated embodiment, the barrel 56 of the cartridge 54 includes an enlarged finger flange 70, such as is commonly used in standardized barrel 56 designs. The cartridge 54 can be pre-filled with a drug or filled at-time-of-use by a user, that is, just prior to placement within the reusable automatic injector 50. Alternate embodiments of cartridges 54 may include, by way of example only, cartridges 54 having a barrel 56 sealed by a plunger seal 64, but having no plunger rod 62.

The housing 52 may optionally be covered by a cartridge cover 72, which may likewise be of any appropriate design. In order to allow the user to view the status of the automatic injector 50, the cartridge cover 72 may be entirely or partially translucent or transparent. Alternately, it may be entirely or partially opaque. The cartridge cover 72 of FIGS. 1 and 2 includes a window 74 that is disposed substantially adjacent the barrel 56 of a supported cartridge 54, allowing the user to view the status of drug delivery. Optionally, the window 74 or portion of the cartridge cover 72 adjacent the window may have dose indication markings to allow the user to identify the drug dose volume contained in the cartridge 54 prior to, during, and/or after drug delivery.

Figure 3:
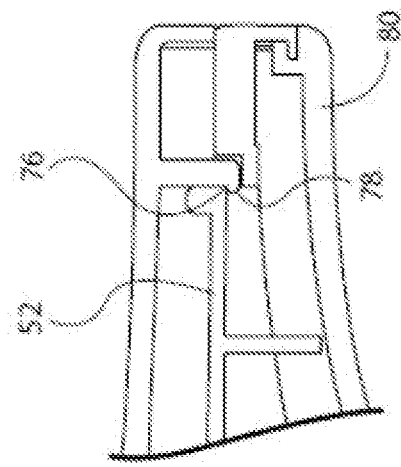
FIG. 3 is a detail view of a latch mechanism of an automatic injector of the present disclosure.

In the illustrated embodiment, the cartridge cover 72 is hinged to the housing 52, although an alternate arrangement may be provided. For example, either the cartridge cover 72 or the housing 52 may include mating protrusions and the other of the cartridge cover 72 or the housing 52 may include detents for receiving the protrusions. Such protrusions and detents may be provided alone, or in conjunction with a hinge arrangement, and may be provided at any appropriate location between the housing 52 and the cartridge cover 72. In one such embodiment, as shown in FIG. 3, a distal detent 76 with mating protrusion 78 may be disposed at or substantially near the distal end of the automatic injector 50 to ensure that the distal end of the cartridge cover 72 is held rigidly to the housing 52, and provide secure closure along substantially the entire contacting surface between the cartridge cover 72 and the housing 52. While the housing 52 and cartridge cover 72 may be formed as separate components, the cartridge cover 72 and the housing 52 may alternatively be formed as a single unit, coupled by a so-called living hinge (not illustrated).

The automatic injector 50 may further include a casing body 80, which provides a smooth outer appearance to the housing 52. The casing body 80 may be formed as a separate structure from the housing 52 that presents an internal chamber that receives the housing 52, or the housing 52 and the casing body 80 may be formed as a single unit. It will be appreciated that, when the automatic injector 50 includes a cartridge cover 72, the cartridge cover 72 may be coupled to the housing 52 by way of the casing body 80. That is, the cartridge cover 72 may be coupled to the casing body 80 which receives the housing 52. As with the housing 52 and the cartridge cover 72, the casing body 80 and the cartridge cover 72 may be formed separately, or as a single unit, connected, for example, by a living hinge (not illustrated).

In the embodiment illustrated in FIGS. 1-4, the cartridge cover 72 is held in a closed position over the housing 52 by a selectively actuable latch 86. In the illustrated embodiment, the cartridge cover 72 includes a protrusion 88 that is received by a recess 90 in the housing 52. A latch release 92 may be slid to the side or depressed to allow the cartridge cover 72 to be latched to or unlatched from the housing 52.

A cartridge sensor 645 (see FIG. 6) may be positioned within the cartridge carrier 126, and may optionally be utilized to sense when a cartridge 54 has been placed within the cartridge carrier 126 of the reusable automatic injector 50. In the illustrated embodiment, the cartridge sensor is disposed at the bottom of the housing 52, although it may be alternately positioned. Placement of the cartridge 54 within the cartridge carrier 126 such that the cartridge sensor senses the presence of the cartridge 54 may provide an indication that permits the reusable automatic injector 50 to be activated/and or activate various operations of the auto injector.

The cartridge sensor 645 may be of any appropriate design. For example, the cartridge sensor may be a mechanical sensor, such that placement of a cartridge 54 into the cartridge carrier causes the displacement of the mechanical sensor. Alternatively, or additionally, the cartridge sensor 645 may be an electrical sensor and/or an electro-mechanical sensor which may be suitably electrically coupled to a main processor system or control unit 605 of the auto injector 50, as discussed below.

Further, actuation of the cartridge sensor, whether electrical or mechanical, may be tied to the operations of the automatic injector 50 such that actuation of the cartridge sensor, for example, allows the cartridge cover 72 to close and latch, or provides a signal to a processor allowing actuation of the automatic injector 50. Upon activation, the motor 106 may cause the transmission assembly 110 to drive the drive screw 114 into the correct position where the plunger interface feature of the plunger carrier 138 is in contact with, or adjacent to, the proximal end of the plunger rod 62 of the cartridge 54. Alternatively, or additionally, a cartridge cover sensor 615 (see FIG. 6) may be utilized to indicate the closing or opening of the cartridge cover 72. Cartridge cover sensor 615 may be an electrical sensor and/or an electro-mechanical sensor which may be suitably electrically coupled to a main processor or control unit 605 of the auto injector 50, as discussed below.

In order to facilitate removal of the rigid needle shield 60, the automatic injector 50 may include structure that engages the rigid needle shield 60 such that movements of the cartridge 54 in the proximal direction results in removal of the rigid needle shield 60. Optionally, a needle shield sensor 625 (see FIG. 6) may be utilized to indicate the removal of the needle shield. Needle shield sensor 625 may be an electrical sensor and/or an electro-mechanical sensor which may be suitably electrically coupled to a main processor or control unit 605 of the auto injector 50.

Depending on the desired injection parameters, the drug may be immediately delivered upon injection of the needle or there may be a momentary delay between the two stages. Such parameters may be programmed into the control system or initiated by the user, as may be desired for operation of the reusable automatic injector 50. In one example, such delay parameters and/or timing parameters may be programmed in the timer unit 630/and or in the storage unit 640 of the auto injector control system 600.

The automatic injector 50 may further include a user interface 96 with features such as an activation button 501 (see FIG. 5A) that may be depressed to initiate operation of the automatic injector 50 or selection of other operative features. Other operative features may include, by way of example only, an identification of the adjustments based upon the needle utilized in the cartridge 54, or volume of medicament carried in the cartridge 54 and the volume to be dispensed, as will be explained in greater detail below. The automatic injector 50 may further include one or more lights 98, speakers (not shown), or the like, indicating the state of operation of the automatic injector 50. It is contemplated that, in some examples, a user may provide operational inputs to the auto injector via voice commands. In such examples, the control system may include a microphone (not shown) to process the voice commands of the user.

Figure 4:
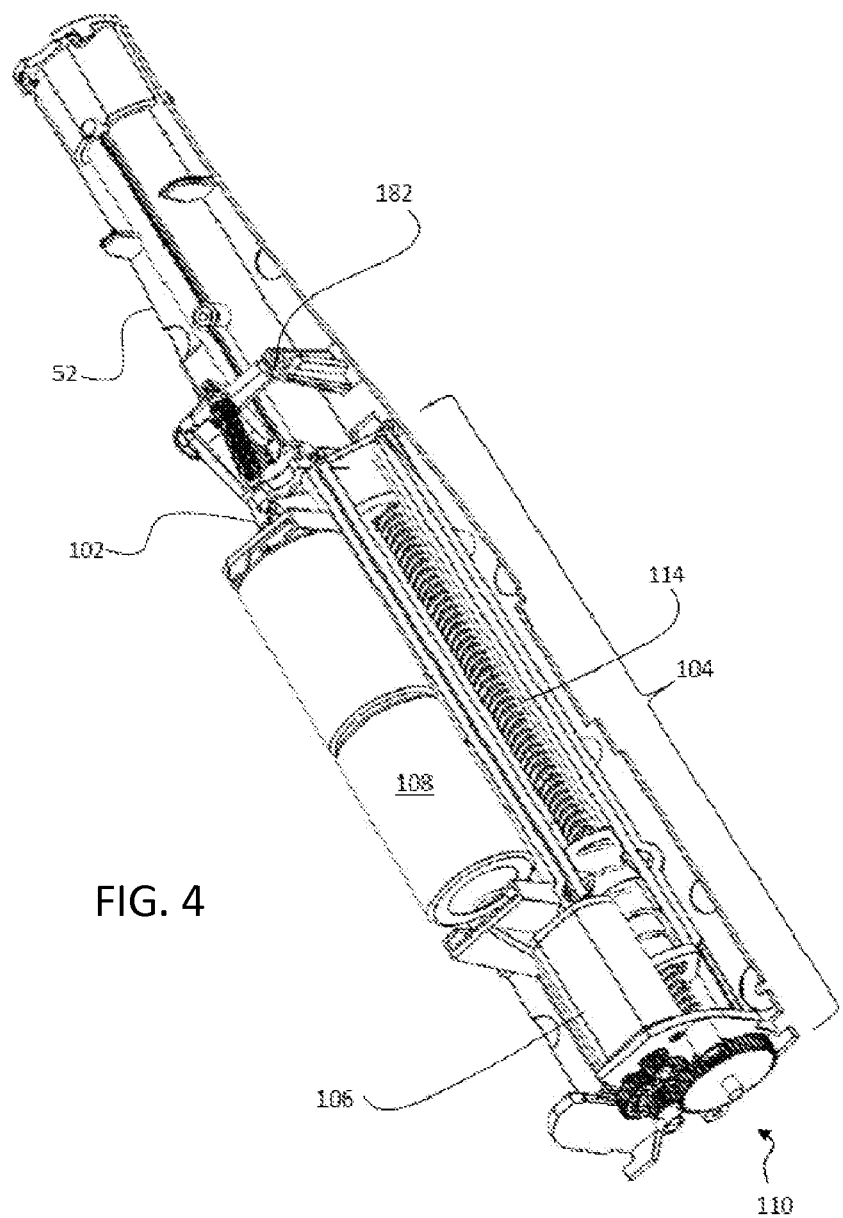
FIG. 4 is an isometric view of a subassembly of an embodiment of an automatic injector of the present disclosure.

The housing 52 may be of any appropriate design, and may be formed as a unitary structure, or it may include a plurality of components. Referring to FIG. 4, the housing 52 is an elongated frame 102 adapted to removably support a cartridge 54 along the upper surface or along structure associated with the housing 52. The housing 52 may further support one or more of the structures associated with the operation or usage of the automatic injector 50. More specifically, in the embodiment illustrated in FIG. 4, the housing 52 additionally supports a drive control mechanism 104 that controls movement of components of the cartridge 54 within the housing 52. The drive control mechanism 104 may be operated by motor 106 powered by an energy source 108. While the motor 106 and energy source 108 are illustrated as being supported on the housing 52, they could alternately be otherwise supported, for example, within a casing body 80. The energy source 108 may be in a number of different configurations and a variety of sources including, for example, disposable batteries, or rechargeable and reusable batteries. A transmission assembly 110 couples the rotary motion of the motor 106 to the drive control mechanism 104.

As discussed below, an electrical drive unit 610 (see FIG. 6) may be electrically coupled to the motor 106 and/or to the drive control mechanism 104 to control the movement of various components of the auto injector 50. Additionally, an energy source or a battery sensor 620 (see FIG. 6) may be utilized to indicate operation capability (e.g., charge remaining of the battery) of the energy source 108. The drive control mechanism 104 described and illustrated herein is for example purposes and may be of any configuration suitable for the application, for example see International PCT App. No. PCT/US2013/049314 which is incorporated herein by reference in its entirety. The status of temperature sensors 520 may be, for example, used as inputs to main control unit 605 that enables and/or disables motor 106 depending on the status of temperature sensors 520.

FIG. 2 shows an embodiment of the present invention in which cartridge 54 (here shown as a syringe but may be any type of drug container or cartridge) is imprinted or labelled with a machine readable tag 820 of information. Tag 820 may be, for example, a bar code, a QR code, a radio-frequency identification (RFID) tag, near-field communication (NFC) tag, or other similar tag or communication protocol known to one having ordinary skill in the art. For simplicity, the term 'tag' is used to encompass such known machine readable labels. Tag 820 may be placed on cartridge 54 at the time of manufacture, time of filling, time of prescription, or any other time prior to drug injection. In at least one embodiment, tag 820 is configured to be read by a remote device suitable for such application, including a smart phone, tablet computer, personal digital assistant (PDA), laptop computer, etc. The information read by the device and/or other information (e.g., date and time of scan) may be stored on the remote device or may be transferred to remote memory such as "cloud" based storage through a Wi-Fi network, cellular network, or any other means. A computer program such as a mobile app may be stored on the remote device to be used when reading the tag 820 as well as to be used to view and/or edit the information collected. The user may read the information contained in tag 820 with such a remote device before or after drug administration. The tag 820 may be placed anywhere on cartridge 54. For example, tag 820 may be placed on barrel 56, plunger rod 62, or plunger head 68.

As shown in FIG. 2, tag 820 on cartridge 54 may be read by a sensor 810 which is a component of automatic injector 50. The reading of tag 820 may be activated through the same mechanism of activation that initiates the automatic injector to perform one or more of removal of needle shield, needle insertion, drug delivery, and needle retraction. Alternatively, tag 820 may be read automatically upon insertion of cartridge 54 (e.g., upon triggering of the cartridge sensor), or tag 820 may be read upon some user action. The sensor 810 may be located internal to the automatic injector. Alternatively, or additionally, the sensor may be located on the outside of the housing 52 or casing body 80 of the automatic injector such that the automatic injector may be used in a similar fashion as the remote device described previously. In one example, the sensor 810 is a wireless data sensor, such as an RFID sensor or antenna, located adjacent the cartridge carrier to identify the cartridge upon cartridge insertion into automatic injector or during operation of the automatic injector. As shown in FIGS. 2, 8A-8E, and 9, the RFID sensor 810 is located on a sensor carriage 850 attachable to the automatic injector 50. Alternatively, the sensor 810 may be mounted directly to the automatic injector 50. The data read by the sensor 810 of automatic injector 50 may be stored in on-board memory contained within automatic injector 50 or may be transferred, wirelessly or through a wired connection and stored on an external or remote device memory. In one embodiment, the data recorded is stored in on-board memory storage 640 as discussed with reference to FIG. 6. The memory storage 640 may optionally be a flash memory source, a solid state memory source, an SD memory source, a hard disk storage device, or any means of storage suitable for the application.

In some embodiments, the information is later uploaded to a computer or server by either the patient or by a physician, nurse, or care giver. In one embodiment the automatic injector is connected to a personal computer (PC), laptop, or other computing device using a connection such as a USB, TCP/IP or Ethernet cable, and/or any suitable wired or wireless connection. Optionally, the information may be stored in memory storage 640, such as an SD memory source which is removable from automatic injector 50. Upon removal of the memory storage unit 640 from automatic injector 50, the memory storage unit 640 may be inserted into or connected to an external device such as a laptop or desktop computer, allowing transfer of the data from the memory storage 640 to the external device. Alternatively, or additionally, the automatic injector 50 may be wirelessly connected to an external device or to a remote memory storage using a wireless connection.

In one or more embodiments the machine readable tag 820 contains information related to the drug container or syringe and/or the drug. This information may include, for example, the drug container or syringe serial or lot number, the drug container or syringe date of manufacture, the type of drug, the date of filling, the drug serial or lot number, the volume of drug contained within the container, the expiration date of the drug, etc. Optionally, a plurality of machine readable tags may be present on the drug container or syringe. The first tag may contain the information related to the drug container or syringe including serial/lot number, date of manufacture, etc. An additional tag may include information related to the drug. In this way, the first tag may be applied at or near the time of manufacture of the syringe or drug container and the second tag may be applied at or near the time of drug filling. Additional information may also be included such as suggested or required dose delivery rate, a suggested or required temperature of the drug or drug container at time of delivery, a unique ID of the automatic injector and/or drug, etc. This information may be used by the main control unit 605 to set various operating parameters. In some embodiments, additional tag may be used so that it can be used or read by other machine or device (e.g., a mobile phone device).

In all embodiments in which transmission of data is provided the transmission of data may be encrypted in order to reduce the risk of the information being accessed by unauthorized users. This encryption may be implemented to protect patient identity and medical records and/or to protect proprietary information concerning the drug or drug delivery device. Additionally, counterfeiting may be difficult because of encryption. The information recorded by the automatic injector may be stored on a server that is remotely accessible by the patient and/or physician, nurse, or care giver. This information may be accessed at the time of a patient visit to a doctor's office, allowing the physician to determine the level of compliance of the patient. Alternatively, or additionally, the data may be accessed at any time by the physician to gauge patient compliance, allowing the physician to follow-up with the patient if the patient is not complying with the prescribed treatment. Optionally, the data may also be accessible by the manufacturer or designer of the drug and/or the manufacturer or designer of the drug container. The data recording and transmission features of the present disclosure may be incorporated into automatic injectors that are intended for single-use, automatic injectors that are intended to be reused, and wearable automatic injectors. It is contemplated that, portions of the data may be accessed based on the identity of the entity (e.g., the manufacturer, physician). That is, an entity may only access certain portions of the data based on the access privilege provided to the entity. This may provide added security and privacy to the data being stored or transferred by the device 50.

One embodiment of the present invention is shown in FIG. 5A. In this embodiment, auto injector 50 includes a temperature control element 650. Temperature control element 650 may be positioned adjacent to or in the close proximity of the drug container or drug cartridge 54. In one example, temperature control element 650 is used to bring the temperature of the drug or drug container 54 into a range of temperature values. For example, the range of the temperature values may be a range of operating temperature values of the drug. The information contained on the tag 820 may include information related to the operating temperature of the drug. The temperature control element 650 may include, but not limited to, polyester flexible heater, thick film metal heater, silicone heater or a resistive polyimide heater. In at least one embodiment, temperature control element 650 is a resistive polyimide heater. In this embodiment a current is passed through a conductive element positioned adjacent to or in proximity to the drug cartridge. The conductive element may, for example, be constructed from a resistive flex circuit. Alternatively, temperature control element 650 may be an incandescent light. The heat given off from the light may be used to heat the drug cartridge 54 or the drug contained in the drug cartridge. Temperature control element 650 may further be any heating element or a combination of heating elements of the same type or different types, known to one skilled in the art. Temperature control element may be designed to provide inductive heating, radiant heating, or convective heating. Temperature control element 650 may be connected to a microprocessor (e.g., control unit 605) of the auto injector 50 via a flexible cable connector 550.

Auto injector 50 in some embodiments includes one or more temperature sensors 520. As shown, in FIGS. 5A-5B, in one implementation, temperature sensor 520 further includes temperature sensor-A 655 and temperature sensor-B 660. Temperature sensor-A 655 and temperature sensor-B 660 (or temperature sensors 520), are positioned to be adjacent to or in proximity to a drug container 54 and to the temperature control element 650; they may be in contact with the drug container 54 when the drug container is installed or may not be, and may be in contact or in close proximity to the temperature control element 650. Sensors 520 may be active sensors or passive sensors. Temperature sensors 520 may take any form suitable for the application. For example, temperature sensors 520 may be infrared thermometer type sensors. These sensors are capable of measuring the temperature of a substance from a distance. This feature may provide increased flexibility in positioning temperature sensors 520. Alternatively, temperature sensors 520 may be radio frequency identification (RFID) sensors which are capable of receiving temperature information transmitted by an RFID chip located in or on the drug container 54. Such RFID temperature sensors may be similar to the sensor 810 useful for reading the data tag 820 and, in at least one embodiment, the functionality of the two sensors may be accomplished by one sensor performing both operations. Alternatively, temperature sensors 520 may be optical sensors which are configured to discern the appearance of a portion of the drug container which changes appearance based on the temperature of the drug container or drug. For example, a strip of color-changing ink may be placed onto the drug container. When the temperature of the drug or drug cartridge reaches a predetermined temperature range the ink changes appearance from a first color to a second color. Temperature sensors 520 may be configured to detect this change in temperature. It is contemplated that, in some embodiments, temperature sensors 520 may include a combination of different types of temperature sensors, as mentioned above.

In one embodiment, temperature sensors 520 may be thermocouples or thermistors (i.e., resistors whose resistances vary significantly with temperature) mounted adjacent to or in close proximity to drug cartridge 54 and to the temperature control unit 650. A thermistor may be a component of an electrical circuit that is configured to have certain characteristics when the thermistor's resistance is in a specific range. This range may be designed to associate with the operational or and/or non-operational temperature range of the drug and of the temperature control element 520. The thermocouple or thermistor sensors 520 may be connected to a microprocessor (e.g., 605 in FIG. 6) which performs or prevents certain actions of the auto injector 50 when the temperature sensors 520 detect that the temperature of the drug and/or the temperature control element 650 are within their respective specified ranges. As described in detail below, in some embodiments, temperature sensor-A or heater temperature sensor 655 may be positioned in close proximity to the temperature control element 650 and may be configured to detect temperatures of the temperature control element or heater 650. Temperature sensor-B or drug temperature sensor 660 may be positioned to be in close proximity to the drug and/or the drug container 54, and configured to detect temperatures of the drug.

Figure 5B:
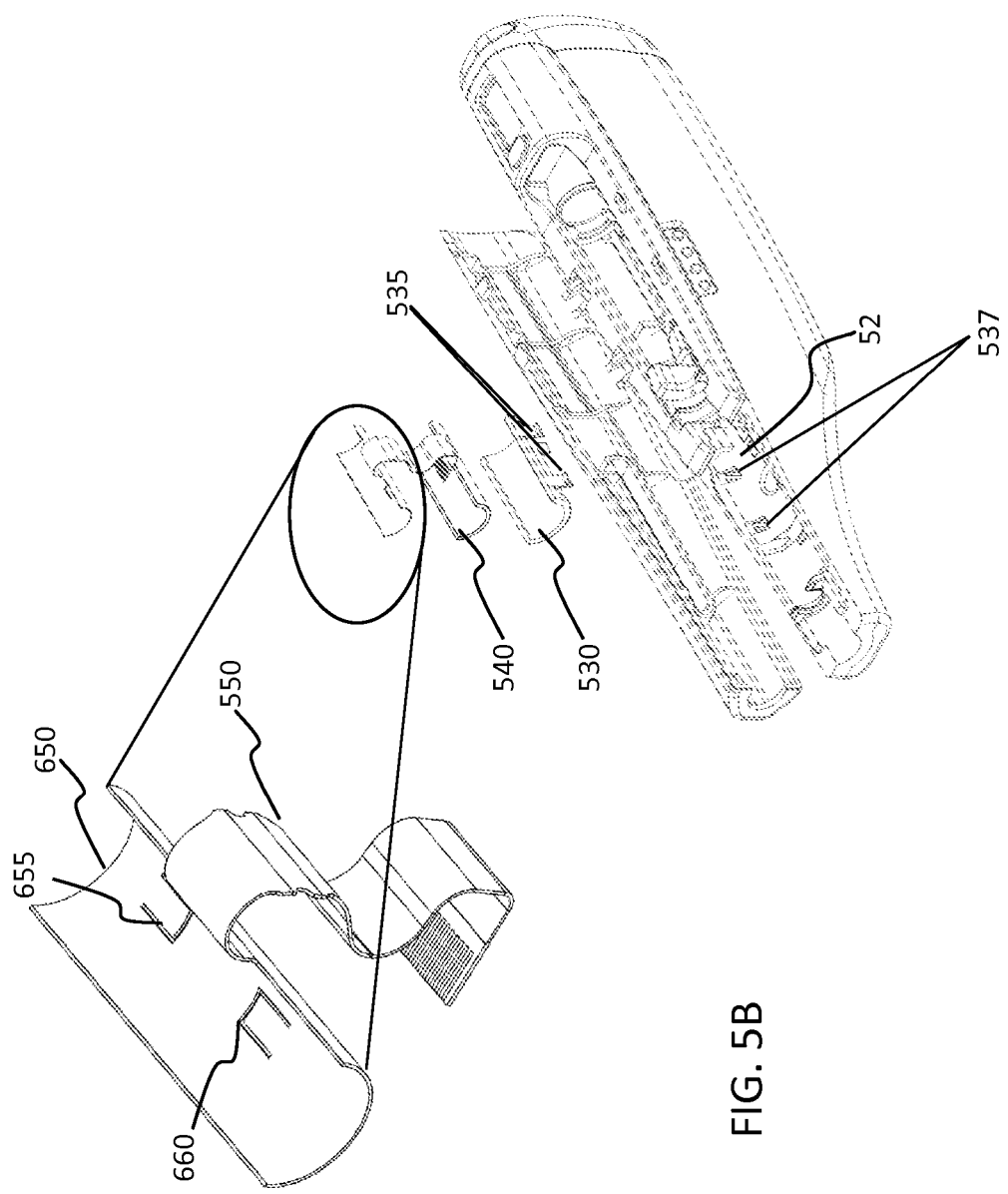
FIG. 5B is a detail of an embodiment of the automatic injector that includes exemplary temperature sensors and an exemplary temperature control element.

FIG. 5B shows an exploded view of one embodiment of temperature control element 650, and the temperature sensors 655, 660 arrangement. The temperature sensors 655, 660 and the temperature control element 650 may be removably positioned on liner 540. These components (655, 660, 650 and 406) may be configured to conform to and fit within housing 52 or cartridge carrier 126 and may sit on a carriage bed 530. Carriage bed 530 may include one or more flexible clips 535 which may engage recesses 537 of housing 52 to securely affix carriage bed 530 to housing 52.

The heater 650 may include an electrical extension cable such as the flexible flat cable (FFC) connector 550. In this way the heater 650 and the sensors 655, 660 may be connected to control unit 605 of the automatic injector (e.g., when the temperature sensors are integral portions of the temperature control element or heater 650). Alternatively, the heater 650 and temperature sensors may be connected to the control unit 605 by their respective connectors. The heater 650 and the temperature sensors 520 may be connected to the control unit 605 by any means known to one skilled in the art including by a soldered wire connection.

The accuracy of the temperature sensors may be chosen to correspond with the requirements of the drug contained in the drug cartridge 54 and the heater 650. Preferably, the accuracy is at least +/−1° C. As shown in FIG. 5B, one or more temperature sensors may be located on the top surface of the heater 650 (i.e., on the surface closer to the drug container). In one example, multiple drug temperature sensors 660 may be utilized (instead of one temperature sensor-B 660) on this surface so that the temperature of the drug container 54 and/or the drug may be measured at more than one location; this may allow the automatic injector 50 to determine that the entire drug and/or drug container has reached a desired operating temperature. Additionally, this may provide redundancy in the case of failure of one of the sensors. As mentioned above, the temperature sensors 660 and 655 may be connected to the control unit 605 through electronic connections incorporated into the heater 650.

Optionally, a polyimide tape (not shown) may be utilized between a cartridge 54 and a top surface of the temperature control element or heater 650 in order to protect the heater and the electronic connections. Polyimide tape may further be used to position and/or secure the components of the temperature sensors and the control assembly (e.g., components in the control system 600 of the auto injector 50. The components of the temperature sensors and controller assembly may additionally, or alternatively, be secured and/or positioned on the carrier bed 530 by any means including adhesives and mechanical fasteners (e.g., screws, rivets, pins, etc.) Optionally, an insulating tape (not shown) may be used to increase the rate of heating of the drug by minimizing the heat that is transferred to the carrier bed, thereby directing the heat to the drug cartridge 54.

Heater 650 may contain etched foil heating elements which allow for the controlled application of heat to the drug or drug cartridge 54. The heater 650 may be flexible and conform to the contour of the housing 52 or cartridge carrier 126 such that it also conforms to the contours of the drug cartridge 54, thereby allowing heat to be applied around the perimeter of the drug cartridge. The liner 540 may be constructed from a foam material to provide protection and/or additional insulation. Liner 540 may include one or more adhesive layers to affix the liner to the carriage bed and/or temperature control element 650. Liner 540 may further include a layer of compliant material which may conform to the contour of the cartridge 54. This may ensure that the sensors 655,660 and temperature control element 650 are in close proximity to the cartridge. The compliant lay may be constructed from an elastomeric, foam, or other compliant material.

In some other embodiments, an external heating device may be provided with the automatic injector 50. The separate heating device may be associated with a charging base that is used to charge the battery of the automatic injector. In this way, the user may place the drug container on or attach the drug container to the separate heating device prior to inserting the drug container into automatic injector 50. A temperature sensor may additionally be associated with the external heating device which may be used to indicate to the user when the drug or drug container has reached the specified temperature. Alternatively, a color-changing ink, as described above, may be applied to the drug container. When the drug or drug container reaches the specified temperature range the appearance of the color-changing ink changes from a first color to a second color, thereby giving the user a visual indication that the drug or drug container is within the specified temperature range.

Furthermore, as shown in FIGS. 1, 5A-5B, in some embodiments, auto injector 50 may include a display unit 635. The display unit may be a liquid crystal display (LCD) thin film transistor (TFT). Display unit 635 may be configured to display texts and/or graphics to provide visual information (e.g., notification) to the user. A user may also provide response to the notification by providing input to the auto injector (e.g., via activation button 501). In some implementations, the user may interact with the auto injector 50 by providing inputs via user touches and/or via a stylus using the display unit 635. In such implementations, the display unit 635 may further include a capacitive or a resistive overlay. The inputs received by the display unit 635 may be processed by the auto injector control system to execute operations of the auto injector 50.

Auto injector may further include activation button 501 that may be depressed to initiate operation of the automatic injector 50 or selection of other operative features.

Moreover, the reusable automatic injector 50 may include one or more control systems (e.g., control system 600) or control units, which may be used to control the timing and parameters of various operations of the automatic injector 50. In one example, the auto injector control system may include an auto injector control unit or the main control unit 605 that may be coupled to the various sensors and components of the auto injector 50. As such, operation of the control system of the auto injector may be based upon feedback from one or more sensors, such as temperature sensors 520 (as shown in FIG. 5B), or inputs received from the user by way of the user interface 96 or activation button 501 or from the display unit 635. For example, the automatic injector 50 may include features that are associated with the closure of the cartridge cover 72 to the housing 52, or the position of the latch release 92. In order to minimize the opportunity for inadvertent actuation of the automatic injector 50 during an operation (e.g., during a warming session of a drug), a cartridge cover sensor 615 may be utilized to signal whether the cartridge cover 72 is open or closed, allowing the control system to prevent actuation (e.g., initiation of warming of the drug) if the cartridge cover 72 is not closed. Similarly, the control system may prevent opening of the cartridge cover 72, that is, movement of the latch release 92, unless the internal components are in one or more particular positions, and/or during a drug warming period.

The control unit 605 of the auto injector 50 may be configured such that one or more operations of the automatic injector are disabled if one of the temperature sensors (e.g., the drug temperature sensor-B 660) detects that the temperature of the drug is not within the specified operational temperature range, and/or the heater temperature sensor 655 detects that the temperature of the heater 650 is at or above, or below an alarm point temperature. In one example, a mechanical interlock (via the drive unit 610) may be operable by an electronic circuit (e.g., the control unit 605) that is connected to or receives input from the temperature sensors 520. In a first position, the mechanical interlock may be configured so that one or more operations, such as, needle insertion and/or needle shield removal, are not able to be activated. In a second position, the mechanical interlock may be configured in such a way that activation is not restricted. When temperature sensor 660 detects that the drug or drug container is within the specified temperature range the control unit may allow or cause the mechanical interlock to be transformed from the first position to the second position (e.g., via the drive unit 610), thereby allowing the activation of the automatic injector.

Automatic injector 50 may further provide an override mechanism which allows the user to activate automatic injector 50 when sensor 660 detects that the drug or drug container is not within the operational temperature range of the drug.

The automatic injector 50 or the control unit 605 of the auto injector 50 may be configured to indicate the temperature of the drug and/or the heater 650. As such, the display unit 635 (coupled to the control unit 605) may then, additionally, operate as a temperature status indicator. Moreover, the display unit 635 may provide notification to the user related to the temperature and warming of the drug process, such as whether the drug is or is not within the operational temperature range. In one example, a light (e.g., a light emitting diode (LED)) (not shown) may be illuminated when the temperature sensor and/or the control unit determines that the temperature of the drug is within the specified operational temperature values.

Additionally, or alternatively, the auto injector 50 may comprise speakers (not shown) to provide an audible alert to the user that the drug is within the specified range.

The operational temperature ranges of various drugs may be set and stored in the storage unit of the auto injector 50, by an administrator during a manufacturing process of the auto injector 50, as described below. Alternatively, the operating temperature range may be contained in tag 820 and be received by the auto injector therefrom.

In one embodiment, temperature sensor 660 and/or temperature sensor 655 may be configured such that it has a first state in which it is actively measuring temperature and a second state in which it is not actively measuring temperature (e.g., upon receiving a command signal from the control unit 605). For example, temperature sensor 660, 655 may be transformed from the second state to the first state upon insertion of the drug cartridge 54 into cartridge carrier 126. This may trigger cartridge sensor 645 to send a status signal to the control unit 605 indicating the presence of cartridge 54 containing a drug. Control unit 605 may then command the temperature sensors to switch from the second state to the first state to initiate detection of the temperatures based on the cartridge sensor signal and also a cartridge cover signal. However, when no drug cartridge is detected the temperature sensors may be in the second state. When in the second state the temperature sensors may consume less power than it does when in the first state. By allowing the temperature sensor to be in the second state when no drug container is installed the battery life of the automatic injector 50 may be increased.

Figure 6:
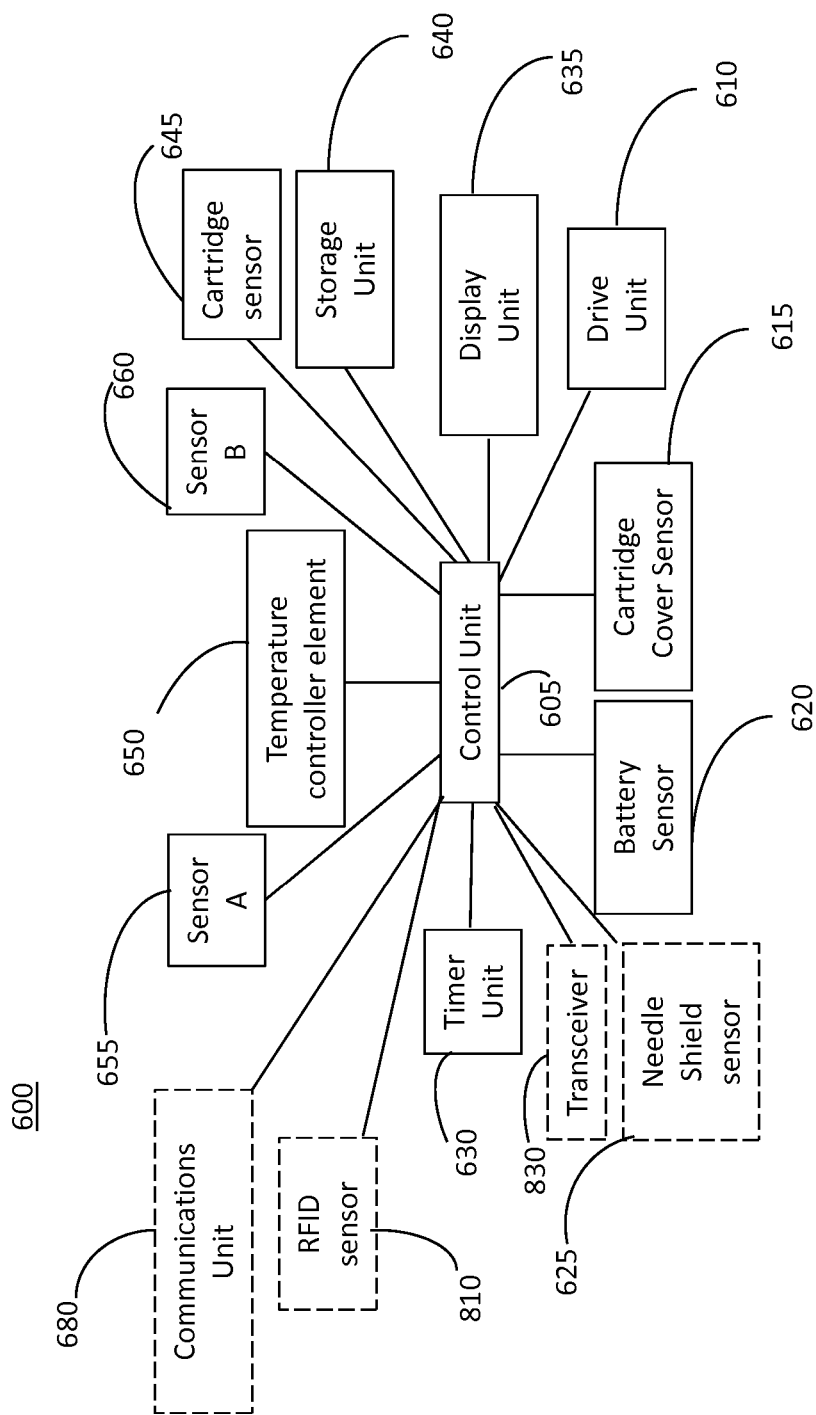
FIG. 6 is a block diagram illustrating an exemplary control system of the automatic injector.

Details are now provided of an exemplary auto injector control system of the auto injector with reference to FIG. 6.

FIG. 6 illustrates a control system 600 that may be included in the auto injector 50. The control system 600 may include one or more control units that are connected to one or more sensors, timers and storage units of the auto injector 50.

In some implementations, the control system 600 may be configured as a temperature control system. In such implementations, the temperature control system may be configured to sense and control temperature of a cartridge containing a drug. The temperature control system may or may not include all the elements of the system 600, and/or may include additional elements. In one example, the temperature control system may be configured for the auto injector 50.

In some other embodiments, the control system 600 may be configured as an identification control system. In such implementations, the identification control system may be configured to identify and/or detect a presence of a cartridge, communicate and/or retrieve information from the cartridge and/or cartridge tag. The identification system may or may not include all the elements of the system 600, and/or may include additional elements. In one example, the identification system may be configured for the auto injector 50. Additionally, in some examples, the auto injector 50 may include one or more control systems, including, but not limited to, the temperature control system and the identification system, and may include additional elements for the operations of the auto injector. Accordingly, the control system 600 may incorporate and be the control system for the temperature control system, the identification system, or both, and incorporate other separate control systems as well.

In some implementations, control system 600 may include a main control unit 605. The main control unit 605 may include one or more controllers, microcontrollers microprocessors, or application specific integrated circuits (ASICs). Main control unit 605 may be implemented as hardware or a combination of hardware and software that may be programmed with instructions. The main control unit 605 may be configured to communicate, for example, by receiving and/or sending signal or data to and from the drive unit 610, cartridge cover sensor 615, energy source sensor 620, needle shield sensor 625, timer unit 630, display unit 635, storage unit 640, cartridge sensor 645, heater temperature sensor or temperature sensor-A 655, drug temperature sensor or sensor-B 660, heater or temperature control unit 650, tag sensor 810, communications unit 680, and transceiver 830. The main control unit 605 may process and interpret the data collected or monitored by the various elements in the one or more control systems in order to determine and execute various functions and operations of the auto injector 50.

The main control unit 605 may be configured to receive feedback from the individual sensors, such as temperature sensors 655, 660, and to cause certain activity of the temperature control unit 650. Additionally, control unit 605 may be configured to cause certain activity of the motor 106 and transmission assembly 110 based on varying feedback from one or more temperature sensors via the drive unit 610.

In at least one embodiment, the main control unit 605 is located at the proximal end of the automatic injector 50 adjacent the transmission assembly 110 and the user interface 96.

According to some embodiments of the invention, the main control unit 605 may be programmed to precisely control the dose of medication administered. For example, when a cartridge 54 includes a larger volume than required for administration, the user may be directed to dispense the unneeded volume prior to, during, or after warming of the drug. In one example, the control unit 605 may obtain the information related to the drug volume from the tag sensor 820 via the RFID sensor 810 and/or via the transceiver 830. Following that, the main control unit 605 via the display unit 635 may prompt the user with a notification to expend the unneeded volume. In response, the user may press the activation button 501 a predetermined number of times to dispense the unneeded volume prior to warming the drug via the heater 650. Accordingly, the automatic injector 50 may be configured to expend or waste a portion of the drug dosage to a reservoir or to the environment, prior to needle injection and drug dose delivery into a user, in order to reduce or adjust drug volume. The temperature of the adjusted volume of the drug may then be detected by the temperature sensor 660 and warmed to a range of operating temperatures of the drug by the control unit (via the heater 650). The automatic injector 50 may then be placed against the injection site, to allow for dose administration.

In some embodiments, drive unit 610 includes electrical circuitry and is electrically coupled to the drive control mechanism 104 which may be operated by motor 106 upon receiving instructions from the main control unit 610. Additionally, drive unit 610 may send signals to the main control unit 605 based on feedback received from the drive control mechanism 104.

In one embodiment, the main control unit 605 may be programmed to administer the programmed volume of medication, and then move the cartridge in the proximal direction to retract the needle from the target tissue by sending command signals to the drive unit 610. The needle may alternatively be removed from the target tissue by automatic retraction of the needle, into the syringe, at completion of drug delivery.

According to some embodiments of the invention, the main control unit 605 of the automatic injector 50 may be configured to command or control predictable movement of a loaded cartridge 54 by sending command signal to the drive unit 610 and optionally receiving response signal from the drive unit 610. In some embodiments, the main control unit 605 may be configured to control repeatable movement, such that the automatic injector 50 may be utilized repeatedly with a plurality of cartridges 54. In those embodiments, in order to inject a patient, the automatic injector 50 may proceed through a plurality of stages that include movement of the needle into a target tissue, administration of an injection by movement of the plunger seal 64, and, optionally, cause or allow needle retraction.

The automatic injector 50 may also include a cover release safety mechanism that prevents the cartridge cover from opening during certain stages of operation. According to at least one embodiment of the present invention, a cartridge cover release safety mechanism may be operated by the main control unit 605 by commanding the drive unit 610 as it progresses through the stages of: syringe cartridge loading, drug warming session, removal of rigid needle shield, needle injection, drug dose delivery, and needle and/or cartridge retraction. In other words, the main control unit 605 permits opening of the cartridge cover only when the needle is not exposed to the user, i.e., during initial loading of the cartridge when the protective needle shield is in place and/or after drug delivery and optional retraction or shielding of the needle. The main control unit 605 prevents opening of the cartridge cover during other stages of operation, e.g., when the needle is exposed for drug delivery, and/or during the warming of the drug. In this way, the cover release safety mechanism operates to inhibit the user's inadvertent exposure to the needle and the heater to reduce or eliminate accidental needle stick injuries or accidental burn of the skin, thus providing highly desirable safety features. Particularly, to ensure cover safety mechanism, in some embodiments, the main control unit 605 communicates with cartridge cover sensor 615.

Cartridge cover sensor 615 may be an electrical sensor that is configured to communicate with the main control unit 605. For example, the main control unit 605 may determine whether the cartridge cover 72 is closed or open based on an operational status signal (e.g., ON/OFF) received from the cartridge cover sensor 615. Based on the determination, the main control unit 605, for example, may initiate or stop operations of the drive mechanism 104 via the drive unit 610. In one implementation, cartridge cover 72 may be a part of the drive control mechanism. As such, the cartridge cover sensor 615 may send or receive signals from the main control unit via the drive unit 610. Cartridge cover sensor 615 may or may not be included in the control system 600.

Energy source sensor 620 may be an electrical sensor that may communicate with the main control unit 605 to indicate charging capacity of the energy source 108 (e.g., how much charge is left in the battery). In one example, that main control unit 605 may receive a command signal from the user interface 96 or activation button 501 that indicates initiation of an operation of the auto injector 50, such as a drug delivery process. Upon receiving the command signal, the main control unit 605 may verify whether the energy source 108 has enough charge to complete a full drug delivery process. The main control unit 605 may consult the energy source sensor 620, or a control unit of the energy source 108 (not shown) to determine the charge capacity of the energy source 108.

Alternatively, or additionally the main control unit 605 may consult the storage unit 640 that may store records of charge capacity information of the energy source 108 from previous drug delivery processes. Based on the determination, the main control unit 605 may provide notifications via the display unit 635 whether to continue the current drug delivery process or charge the energy source prior to initiation of the current drug delivery process or sequence. Battery sensor or energy source sensor 620 may or may not be included in the control system 600. Additionally, energy source sensor 620 may be consulted by the control unit 605 to determine whether there is sufficient charge in the energy source 108 to warm the drug using the temperature control unit 650. Yet in another example, the control unit may additionally consult the tag 820, tag sensor 810 and the transceiver 830 to obtain information related to the warming time of the drug. Based on the information related to warming time of the drug and charge remaining in the energy source, the auto injector 50 may notify the user whether the auto injector 50 needs to be charged prior to the drug delivery and/or warming of the drug.

The needle shield 60 may be a part of the drive control mechanism, and may include structure to engage the rigid needle shield 60 such that movements of the cartridge 54 in the proximal direction results in removal of the rigid needle shield 60. This may cause the drive unit 610 to send signals to the main control unit indicating a removal of the needle shield. Based on the determination, the main control unit 605, for example, may initiate or stop operations of the drive mechanism 104 via the drive unit 610, during or prior to a drug delivery process. Optionally, needle shield sensor 625 may be an electrical sensor that is configured to communicate with the main control unit 605. For example, the main control unit 605 may determine whether the needle shield 60 is removed or in position on the syringe needle based on an operational status signal (e.g., ON/OFF) received from the needle shield sensor 625. Needle shield sensor 625 may or may not be included in the control system 600.

Timer unit 630 may be a digital clock that may be programmed, for example, to set up time periods for various operations of the auto injector 50. For example, the timer unit 630 may be configured to indicate, to the main control unit 605, a time-out period for an operation (e.g., predetermined drug warming period or session, wait time after cartridge placement, etc.) or a delay period between operations (e.g., a time delay between the closing of the cartridge cover 72 and the initiation of the drug warming). In some embodiments, timer unit 630 may directly communicate with the control units of various sensors. In some implementations, the timer unit 630 may be included in the main control unit 605.

Display unit 635 may be a LCD TFT. Display unit 635 may be electrically coupled to the main control unit 605 and may receive instructions (from the main control unit 605) to display texts and/or graphics to provide visual information (e.g., notification) to the user. A user may provide response to the notification by providing input to the auto injector (e.g., via activation button 501 and/or by interaction with display unit 635).

The display unit 635 may prompt the user to provide input for carrying out certain operations of the auto injector 50 via the display unit 635. In that example, the display unit 635 may include a graphical user interface and/or touch screen interface that may be configured to receive inputs or instructions from the user (via user touches and/or via a stylus). The display unit may further include a capacitive or a resistive overlay.

In one example, the display unit 635 may provide menu options, so that the user may choose and modify various settings of the auto injector 50. Additionally, the menu options may be categorized in multiple screens, such as a home screen and a settings screen. Home screen may display options related to a current cartridge operations (e.g., verification of insertion of the cartridge in the carrier 126 and verification whether the cartridge cover is closed). In one example, the home screen may provide options related to the drug warming. For example, one of the options may include prompting the user to warm the drug or drug cartridge upon inserting the cartridge in the carrier 126. Settings screen, on the other hand, may provide menu options such as, language settings, speed settings of the injection, etc., of the auto injector 50.

The inputs received by the display unit 635 may be processed by the main control unit 605 to execute operations of the auto injector 50. For example, upon being prompted to warm the drug (in the home screen) as discussed above, the user may choose to initiate drug warming by choosing a yes option (not shown). Alternatively, the user may opt-out or skip the warming of the drug by selecting an opt-out option. It is noted that, the display unit 635 may or may not be included in the control system 600.

Control system 600 may include storage unit 640. Storage unit 640 may include one more storage units, such as a random access memory (RAM) or other dynamic storage device, and/or a read only memory (ROM), and/or an electrically erasable programmable read only memory (EEPROM) for storing temporary parameters, information and instructions for the main control unit 605. In some implementation, the storage unit may be implemented as a non-transitory computer readable medium which stores instructions that may be processed and executed by the control unit to control operations of the control system of the auto injector. Additionally, storage unit 640 may store error codes or error notification for various operations associated with the sensors and control unit of the auto injector 50. The error codes may be pre-programmed into the storage unit 640, for example by an administrator of the auto injector 50. In one example, main control unit 605 may retrieve the appropriate error codes, based on an error signal received from a sensor, and may further indicate an error notification to the user (e.g., via the display unit 635) related to the sensor.

In at least one embodiment, the storage unit 640 may store error codes related to drug warming and temperature detection. For example, the main control unit may access the appropriate error codes to notify the user via the display unit 635. For example, if the heater 650 overheats the drug, an appropriate error code may indicate that the drug has been overheated. Additionally, if the initial detected temperature of the drug or drug container 54 (i.e., prior to the warming of the drug) is above or below an alarm point temperature, appropriate error code may indicate that the cartridge is either too hot or too cold.

Storage unit 640, may additionally, store predetermined drug warming time periods for various drugs. In one example, if the control unit 605 determines that the heater 650 has warmed a drug beyond its predetermined warming time period, the control unit may provide an error notification, and/or shut down the auto injector. Additionally, range of operational temperature values of the various drugs may be stored in the storage unit. In one example, the range of operational temperature values, the predetermined drug warming time periods, viscosity values, drug IDs and other appropriate drug information may be stored in various drug profiles of the respective drugs. As discussed below, in some examples, the drug information may be received from the tag 820 via the tag sensor 810.

In some embodiments, the error codes and the drug profile for various drugs may be pre-programmed and stored in the storage unit by an administrator during the manufacturing process of the auto injector 50 and may be preferably accessed by the control unit 605. Alternatively, such information may be obtained by the auto injector 50 from the tag 820 via the tag sensor 810 of an identification system.

In some embodiments, the auto injector 50 may further include a data tag sensor or a cartridge ID sensor 810 (referred to herein as a "tag sensor") that may be coupled to the control system and/or to the control unit and configured to read or scan a syringe or cartridge tag 820 (referred to herein as a "syringe tag" or "tag"). In some embodiments, the tag sensor 810 may communicate with the control unit 605 via a receiver and/or a transceiver 830 that is capable of transmitting and receiving data. In some examples, transceiver 830 may monitor and/or transmit the signal characteristics and/or data that are received via the tag sensor 810. The control unit may receive data/information from the tag sensor via the transceiver 803. In some embodiments, the transceiver 830 may perform communication signal processing operations such as, modulation/demodulation operations.

The syringe tag may be associated and provided on the cartridge 54. The syringe tag 820 may be associated and/or provided on the cartridge 54 as shown in FIGS. 8A-8E. The syringe tag may include information such as a drug profile of the drug contained in the cartridge 54. For example, the drug profile may include information, such as, but not limited to, drug ID (e.g., an unique identity of the drug contained in the cartridge 54), drug volume information, drug viscosity information, drug temperature information, drug warming period and/or drug expiration date, manufacturing ID, lot number etc. The drug tag may be encoded into, but not limited to, a bar code, a quick response (QR) code or a RFID tag.

The tag sensor or the cartridge ID sensor 810 may be configured to scan or read the drug tag and decode the drug tag. For example, the tag sensor may be a bar code scanner, a QR code scanner, an interrogator, an antenna or any other scanner or reader known to an ordinary person skilled in the art, which may suitably scan or read the drug tag, as discussed with reference to FIGS. 8A-10.

In some examples, the control unit 605 may receive the data of the cartridge tag 820, from the tag sensor 810 via the transceiver 830. In such examples, the control unit 605 may consult a code/decode or an encrypt/decrypt module (not shown) of the control system 600 to decode data of the syringe tag 820. The code/decode module may store various coding/decoding schemes, and the main control unit may access the appropriate decoding scheme to decode the drug tag. In some examples, code/decode module may be included in the control unit 605. Additionally, or alternatively, the tag sensor 810 and/or transceiver 830 may directly decode or decrypt the data received from the tag 820.

Yet in another implementation, the auto injector 50 may perform verification of the identification of the drug externally. In that implementation, the control unit 605 may receive a coded syringe tag information and may further consult an external computer device such as, a cloud server (not shown), or a user equipment (UE) device (e.g., a mobile telephone device) (not shown), to decode the syringe tag. In such implementation, the main control unit 605 may communicate with the external server or the UE device via the communication unit 680. The communication may include, but not limited to, sending of the syringe tag information to the external computer device, and in response, receiving a decoded syringe tag, and/or a drug profile of the drug.

In some examples, control system 600 may include communication unit 680. Communication unit 680 may include one or more 802.11 Wi-Fi transceivers, a cellular transceiver, IEEE 802.14 ZigBee transceiver, a Bluetooth transceiver, and/or a Bluetooth Low Energy (BLE) transceiver. As described above, the auto injector 50 may communicate with the external computer device, and/or with the syringe tag via the communication unit 680. In some implementations, the auto injector 50 may include appropriate transceivers to communicate with the external computer device and/or the syringe tag via wireless communication protocols, such as near-field communication (NFC), infrared or ultrasonic.

In some implementations, the control unit 605 may cause the tag sensor 810 to scan the syringe tag 820 to access the drug profile information of the drug. Based on the scan, the control unit 605 may access the drug profile of the drug (e.g., prior to, and/or after the drug tag has been decoded).

In one example, the main control unit 605 may identify the drug ID that is included in the drug profile. For example, the main control unit may compare the received drug ID (based on the scan) with a plurality of drug IDs that may be stored in a lookup table or a database in the storage units of the auto injector 50. Based on the comparison, the main control unit 605 may determine that the scanned drug ID is identified or recognized, when there is a match between the scanned drug ID and one of the stored drug IDs. The main control unit 605 may then cause the display unit to display appropriate notification indicating that the drug or the drug cartridge 54 is identified.

The main control unit 605, may receive other drug profile information (e.g., based on the scan) of the identified drug, and may cause various activities associated with the delivery of the drug. For example, based on the warming period, operational temperature range, volume, and/or viscosity information of the drug, the main control unit 605 may set appropriate operation parameters (e.g., control loop parameters) and cause the temperature sensing and control elements to warm the drug to its operational temperature within the predetermined time, as described elsewhere herein.

In another example, the syringe tag information may only include a drug ID. As such, the main control unit 605 may identify the drug based on the drug ID, as discussed above, and then retrieve the corresponding drug profile information (e.g., warming period, operational temperature range, volume, and/or viscosity information and error codes) from the storage unit 640, or from an external computer device for the identified drug. Based on the retrieved information, the control unit 605 may set the control loop parameters to warm the drug to its operational temperature range, as described elsewhere herein.

In at least one embodiment, the tag sensor 810 is a radio frequency ID (RFID) sensor 810 as shown in FIGS. 8A-8E. In one example, the control unit 605 may cause the RFID tag sensor 810 to scan the syringe tag 820 to access the drug profile information of the drug (e.g., via the transceiver 830). As discussed above, placement of the cartridge 54 within the cartridge carrier 126 may cause the cartridge sensor 645 to send a signal to the main control unit 605 indicating the presence of the cartridge 54. Based on the received signal, the main control unit 605, for example, may activate certain operations of the auto injector 50. In at least one embodiment, the presence or identification of the cartridge 54 based on the cartridge sensor 645 (alone, after, or in combination with the cartridge cover sensor 615 signaling that the cartridge cover 72 is closed) may trigger activation of a tag sensor 810.

The tag sensor 810 may be mounted directly onto the surface of the housing 52, such as internal housing surface 52A, or onto a sensor carriage 850 which is then mounted onto the housing 52. The latter configuration may provide ease of assembly since the sensor carriage 850 and tag sensor 810 may become a modular sub-assembly for integration into the device 50 when such capabilities are desired.

Figure 8A:
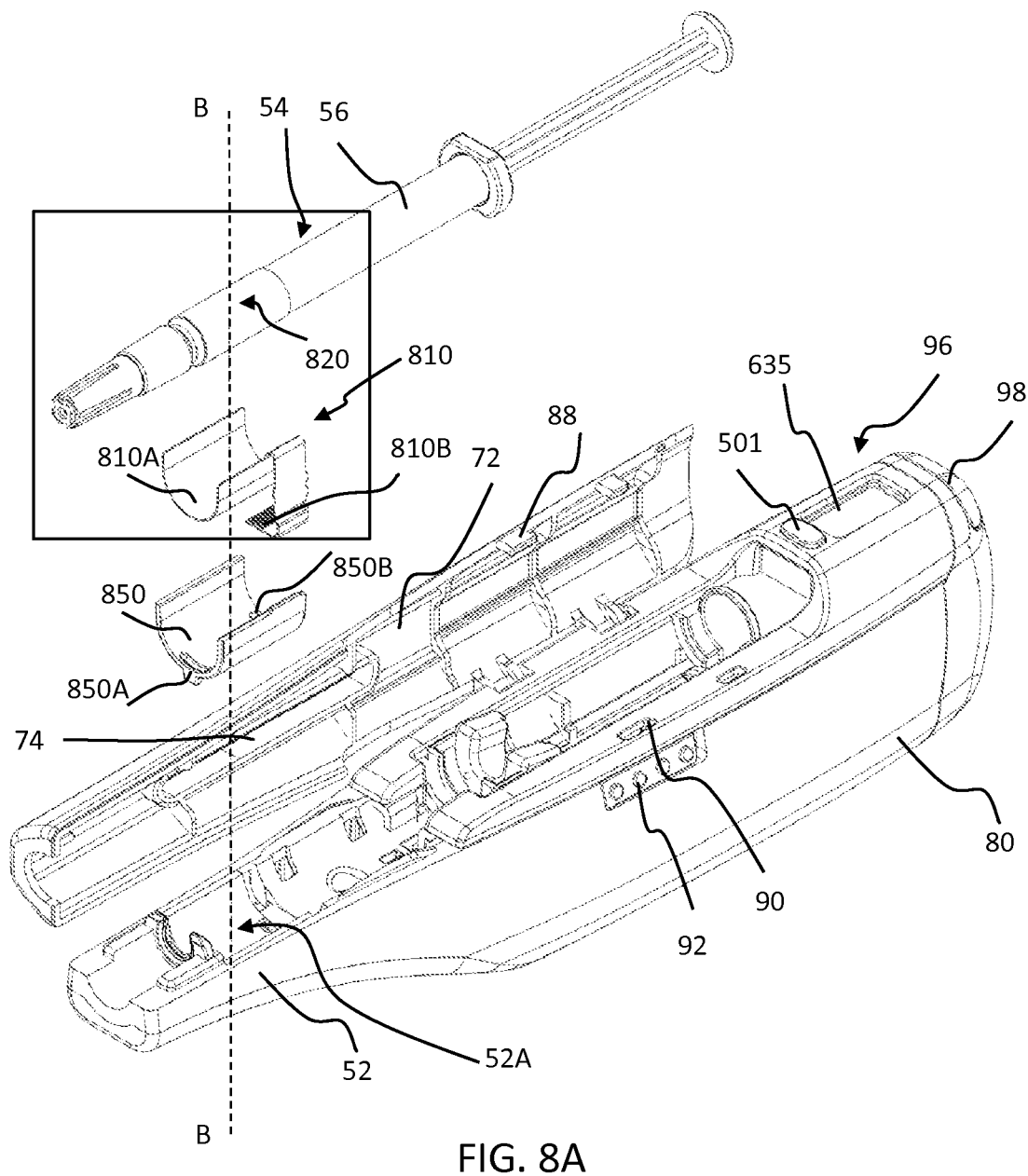
FIG. 8A is a partially exploded isometric view of the embodiment shown in FIG. 2.

FIG. 8A shows a partially exploded view, along axis 'B', of the cartridge 54, the tag sensor 810, and the optional sensor carriage 850. As shown in FIG. 8A, the sensor carriage 850 may have snap prongs 850A, 850B, or other similar features, to permit ease of assembly and mounting onto the housing 52, such as at internal housing surface 52A.

Figure 8C:
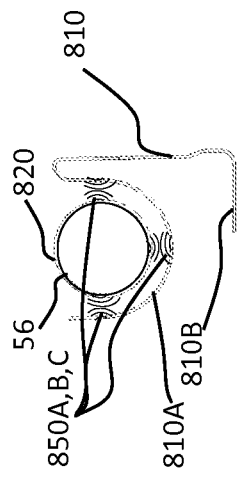
FIG. 8C is a cross-section view along axis 'B' of certain components shown in FIG. 8A.
Figure 8D:
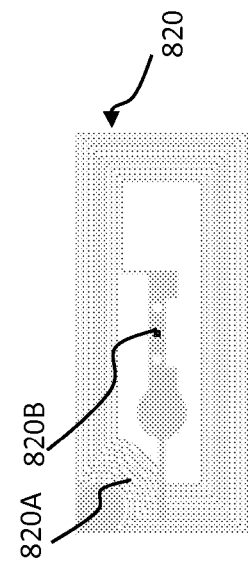
FIG. 8D is an exemplary embodiment of an RFID tag or inlay attachable to a syringe or cartridge, as shown in FIG. 8A.
Figure 8E:
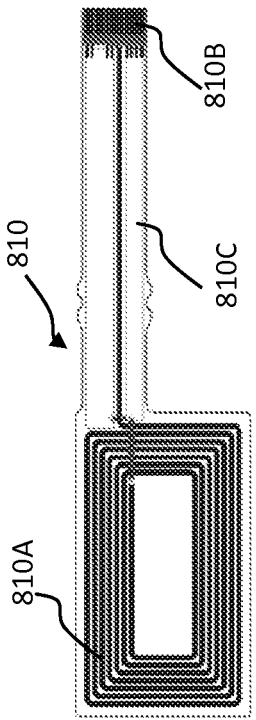
FIG. 8E is an exemplary embodiment of an RFID antenna or sensor attachable to a sensor carriage, as shown in FIG. 8A.
Figure 8B:
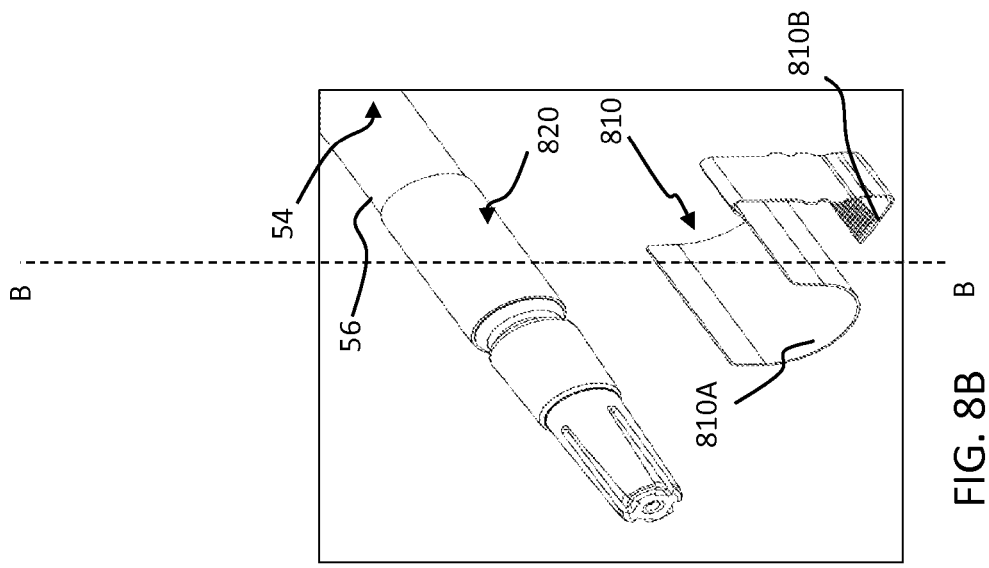
FIG. 8B is an enlarged view of certain components shown in FIG. 8A.

FIG. 8B shows an enlarged isometric view of a portion of certain components shown in FIG. 8A. In this embodiment, the tag 820 is affixed to the barrel 56 of cartridge 54. The tag 820 may be affixed in a number of known methods, including but not limited to by adhesion or glue.

In at least one embodiment, the tag sensor is an RFID sensor or antenna that may send a signal to identify a cartridge that contains a drug, and/or a cartridge tag 820, or specifically an RFID tag, for example based on the information on the tag. Moreover, tag 820 may be a passive tag that does not require its own built-in power source and enables data transmission when positioned in the field of an interrogator antenna or sensor 810. Such configurations may be economical and may provide a smaller assembly size. It is contemplated, however, in some embodiments, the RFID tag may be an active tag with a built-in power source that permits the RFID tag to send a signal itself. In such scenarios, appropriate sensor 810 may be implemented to communicate with the active RFID tag.

FIG. 8D shows exemplary embodiments of an RFID tag 820 or inlay attachable to a syringe or cartridge 54, as shown in FIGS. 8A-8B. In one example, tag 820 may include one or more antenna conductor traces 820A and an integrated circuit (IC) 820B. The RFID tag 820 may be a passive element, and as such may not require internal power source to be operational or activated.

In one example, the tag sensor 810 may communicate with the tag 820. The communication between the tag sensor 810 and tag 820 may be contactless communication (e.g., a wireless communication). For example, the tag sensor 810 may transmit an interrogating signal which may excite or activate the tag 820. In one example, the interrogating signal may be a radio frequency (RF) signal operating at a frequency of 13.56 Megahertz (MHz). It is noted that, operating at such a frequency may advantageously provide an appropriate operating distance within which the tag sensor 810 may access the data information from the tag 820. The interrogating signal upon being detected by the tag 820, may provide sufficient power for the IC 820 to power up and transmit back a response signal that includes data and information pertaining to the drug or drug cartridge (e.g., drug profile).

In one example, the data or information (e.g., drug profile) may be stored in a storage unit (e.g., in a non-volatile memory) (not shown) of the tag 820. The stored information may include information related to the cartridge, and/or drug contained in the cartridge, and other operational protocols or parameters. It is contemplated that, in some implementations, at least some portions of the data may or may not be overwritten. For example, read-only data may not be over-written, whereas, other data may be over-written by the tag sensor 810 or the auto injector 50. As discussed above, in some embodiments, the data stored in the tag 820 may be encoded/encrypted which may advantageously provide security and/or privacy to the user.

FIG. 8E is an exemplary embodiment of an RFID antenna or sensor 810 attachable to a sensor carriage 850, as shown in FIG. 8A, or directly to the housing 52. Such sensor 810 includes one or more sensor antenna traces 810A and a connection point 810B at an end of an antenna feed line that is configured for connection to a control systems or aspect thereof, such as a flex connector. In one example, a feedline 810C may couple the antenna traces 810A to the connection point 810B. 810A shows multiple loop or traces, however, it is contemplated, that in one example, a single loop or trace may be used. As discussed above, in one implementation, the tag sensor 810 may emit the interrogating signal to activate the passive tag 820, and in response, receive data or information that is stored in the tag 820. Additionally, tag sensor 810 may directly decrypt or decode the data received (e.g., a drug profile) from the tag 820 which may be transmitted to the main control unit 605. In some embodiments, the tag sensor may consult a decryption/encryption module (not shown) of the control system to decrypt the data received from the tag 820.

Alternatively, in some embodiments, the main control unit 605 may receive the encrypted data from the tag sensor (e.g., via a transceiver), and may then decrypt the data (e.g., upon consulting the decryption/encryption module) to activate and/or set parameters associated with various operations of the auto injector 50.

FIG. 8C is a cross-sectional view along axis 'B' of certain components shown in FIG. 8A. As shown, in at least one embodiment of the present invention the tag 820 and sensor 810 are in a substantially concentric arrangement in the portions that engage for data communications. It is noted that, the concentric engagement may provide enhanced interaction that may be substantially similar to a planar engagement (not shown) between the tag 820 and the sensor 810. That is, in the concentric configuration, the corresponding antenna conductor traces 820A of tag 820 and the antenna traces 810A of sensor 810 are aligned in a manner which is substantially similar as if those components were in flat parallel planes (e.g., lying on top of each other).

Moreover, due to the arcuate assembly of the sensor 810, it is noted that, the sensor 810 may emit electromagnetic fields (e.g., during the transmission of the interrogating signal) in a manner that may effectively stimulate the tag 820 and receive data from the tag, for example when the syringe or cartridge 54 possess a curved tag 820.

FIG. 8C shows an exemplary engagement or coupling of the electromagnetic fields emitted from the tag 820 and the corresponding electromagnetic fields emitted from the sensor 810 due to the concentric alignment of these components. The tag 820 and the sensor 810 couple electromagnetically with each other. In one example, the coupling is an inductive or a magnetic coupling.

The sensor 810 communicates with the tag 820 through a continuous engagement or coupling because of the substantially concentric alignment of the tag 820 and sensor 810 (the multiple points 850A, B, C are shown for illustration purposes only and it is noted, that the electromagnetic fields are continuous between tag 820 and sensor 810). It will be appreciated, that the concentric configuration may allow a user to instantly load the cartridge on the auto injector without the need to be aware of the orientation of the tag with respect to the sensor 820. Additionally, because the concentric configuration provides instant and direct alignment between the tag 820 and the sensor 810, the auto injector may not need any additional mechanical indexing or alignment features or components.

It will be appreciated, that such an alignment can improve the data communications between the tag 820 and the sensor 810, ensuring reliable data collection of the drug ID, operational parameters, and other information that may be stored on the tag 820.

Although, as discussed above, the drug information may be received by the auto injector from the tag 820 via the tag sensor 810, however, it is contemplated that, in some embodiments, a user may manually provide drug information via the activation button (e.g., pressing the activation button a predetermined number times) and/or via the display unit 635 by touch inputs to provide necessary drug information (e.g., drug ID, etc.) Based on the inputs received, the main control unit 605 may identify the drug and access the corresponding drug profile from the storage unit 640, in order to carry out various operations for the drug delivery.

Referring back to FIG. 6, in some embodiments, the device 50 may include a cartridge sensor 645 that may be electrically or electromechanically coupled to the main control unit 605. As discussed above, placement of the cartridge 54 within the cartridge carrier 126 may cause the cartridge sensor to send a signal to the main control unit indicating the presence of the cartridge 54. Based on the received signal, the main control unit 605, for example, may activate certain operations of the auto injector 50 (e.g., initiate the heating of the drug by sending a command signal to the temperature control element 650). Cartridge sensor 645 may or may not be included in the control system 600.

Temperature control unit or heater 650 may be electrically coupled to the control unit 605 (e.g., via flex cable connector as shown in FIG. 5B). Control unit 605 may send command signals (e.g., pulse width modulated signals) to the heater 650, based on which the heater 650 may warm up the drug or drug cartridge 54. In one example, the control unit 605 may send command signals to control the warming of the drug (via the heater 650) based on the temperature feedback received from the heater temperature sensor 655 and the drug temperature sensor 660. In one example, the main control unit may access and process the drug profile information of a drug (e.g., operating temperature values of the drug, predetermined warming time of the drug, volume, viscosity, etc.) to initiate the warming of the drug via the heater 650.

In some embodiments, heater sensor 655 may be electrically coupled to the control unit 605. As discussed above, heater sensor 655 may be positioned in close proximity to the heater 650 (as shown in FIG. 5B). Heater sensor 655 may be configured to detect a range of temperature values of the heater 655 and send the detected temperature values to the main control unit 605. Additionally, heater sensor 655 may be configured or programmed to store one or more alarm temperature values in a storage unit (not shown) of the heater sensor. In one example, when the heater sensor 650 detects a temperature of the heater 650 that is above an alarm temperature value or below another alarm temperature value, an alarm set pin (not shown) may be triggered in the heater sensor 650. The heater temperature sensor 655 may then send an alarm signal to the control unit 605. The main control unit may then cause the display unit to display an error signal. Heater temperature sensor 655 may be configured to monitor a range of temperature values of the heater prior to and during a warming period of a drug and provide temperature feedback to the control unit 605. Accordingly, the control unit 605 may then adjust the temperature of the drug to an operating temperature and/or to a range of operating temperature values of the drug.

In some embodiments, drug or drug cartridge temperature sensor 660 may be electrically coupled to the control unit 605. As discussed above, drug temperature sensor 660 may be positioned in close proximity to the drug and/or to the drug cartridge 54 (as shown in FIG. 5B). Drug temperature sensor 660 may be configured to detect a range of temperature values of the drug and send the detected temperature values to the main control unit 605. Additionally, drug temperature sensor 660 may be configured or programmed to store one or more alarm temperature values in a storage unit of the drug temperature sensor (not shown). In one example, when the drug temperature sensor 660 detects a temperature of the drug that is above an alarm temperature value or below another alarm temperature value, an alarm set pin (not shown) may be triggered in the drug temperature sensor 660. The sensor 660 may then send an alarm signal to the control unit 650. The main control unit may then cause the display unit to display an error signal. Sensor 660 may be configured to monitor a range of temperature values, including the operating temperature values of the drug, prior to and during a warming period of the drug, and provide temperature feedback to the control unit 605. Accordingly, the control unit 605 may then adjust the temperature of the drug to an operating temperature and/or to a range of operating temperature values of the drug.

In at least one implementation, control unit 605 may be configured to be a Proportional-Integral-Derivative (PID) controller that controls the heater or the temperature control element 650 by a feedback loop, for example to adjust (e.g., to warm up) the drug temperature to an operating temperature of the drug. In such an implementation, the temperature sensors 655 and 660 detect the temperature of the heater 650 and the drug, respectively, and send output signals based on the detected temperature to the control unit 605. For example, control unit 605 receives an output signal from the drug temperature sensor 660 and determines whether the received temperature value of the drug is within a range of operating temperature values of the drug. Based on the determination, the PID controller or control unit 605 then controls the heater 650. In one example, the control unit 605 may consult the range of operating temperature values of the drug that is stored in the storage unit 640 or receive those operational values from the tag 820 or drug ID (as described herein) to perform the determination.

Control unit 605 may send command signals, for example, via modulated electric current or voltage signals to the heater 650 to increase the temperature. Moreover, the sensor 655 (that is located in close proximity to the heater 650) may detect the increased temperature of the drug and further send a feedback signal to the control unit 605. Based on the feedback signal received from the heater temperature sensor 655, the feedback control loop of the control unit 605 may further modify or adjust the temperature or heating characteristic of the drug via the heater 650.

Furthermore, the adjustment of the temperature by the control unit 605 may include an appropriate increase or a decrease in the temperature of the drug or the drug container 54. For example, the temperature sensors 655 and 660 may periodically determine subsequent temperature readings, and the feedback control loop of the control unit 605 may intermittently or continuously adjust the temperature of the heater 650, until the operational temperature of the drug is achieved within a desired degree of uncertainty, for example, ±2.5° C. or ±1° C. of the operational temperature (based on the temperature feedback from the sensors). During the adjustment process, the PID control unit may constantly access and compare the stored operating temperature values of the drug.

It is noted that, a drug may have a range of operating temperature values that is bounded by an upper limit and a lower limit. The limits may be calculated as percentages of the operating temperature value of the drug. These values may be pre-programmed in the storage unit 640, as discussed above.

In one example, the PID controller/control unit 605 may consult the timer unit 630 to ensure that the adjustment of the drug temperature to the operating temperature is achieved within a predetermined time (e.g., a time provided in the drug profile of the drug). Additionally, the detected temperature values may be received or determined by the control unit 605 in a predetermined time interval, (e.g., between every 30 seconds). In one example, the parameters of the feedback controller, such as the P, I and D may be controlled or adjusted appropriately in order to meet particular requirements, such as the time to reach the optimal temperature. In another example, the parameters may be adjusted appropriately so that the adjusted temperature lies within a range of the operating temperature values. It is contemplated that appropriate controls may be achieved by using or not using one or more PID parameters. Alternatively or additionally, other control loop feedback algorithms, known to one skilled in the art, may be programmed in the main control unit 605 instead of implementing a PID controller alone.

It is contemplated that the temperature sensing elements 655 and 660 and the temperature controlling element 650 of the temperature control system and/or the identification system of the present invention may be used with wearable automatic injectors as described in PCT/US2012/53174, PCT/US2013/057259, U.S. Pat. No. 8,939,935, PCT/US2012/054861 and PCT/US2013/057327.

FIG. 9 is an isometric view of another embodiment of the automatic injector 50 containing both a temperature sensing and temperature control element 520 and a data communications element, such as an RFID antenna or sensor 810.

The details focusing on FIG. 10 below provide discussion for the integration of such elements together, with reference to a flow chart 900 showing an exemplary method for communicating information between tag 820 and tag sensor 810.

Figure 7A:
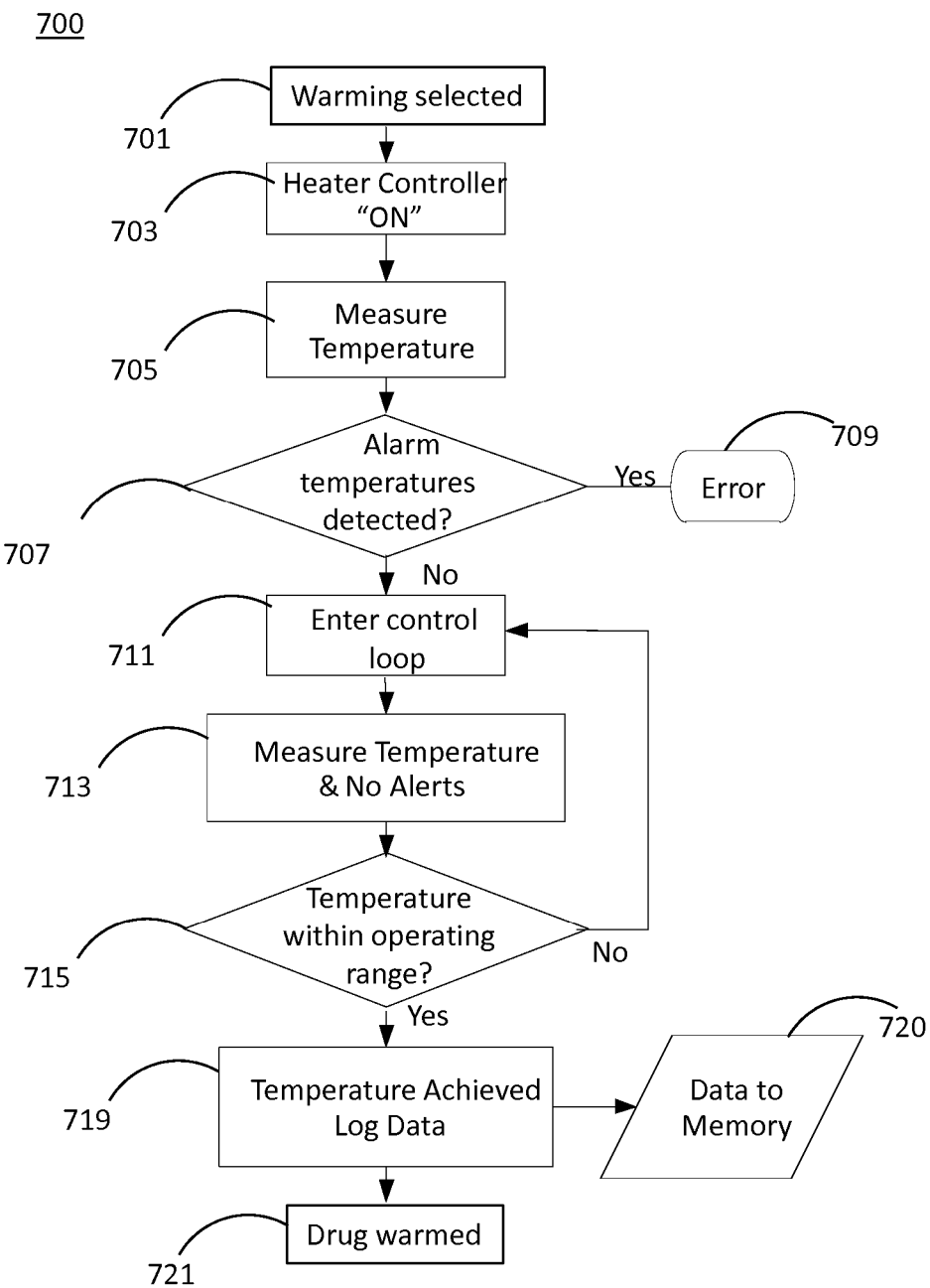
FIG. 7A is a flow chart illustrating an exemplary method for warming a drug product or a drug cartridge containing the drug product of an automatic injector.
Figure 7B:
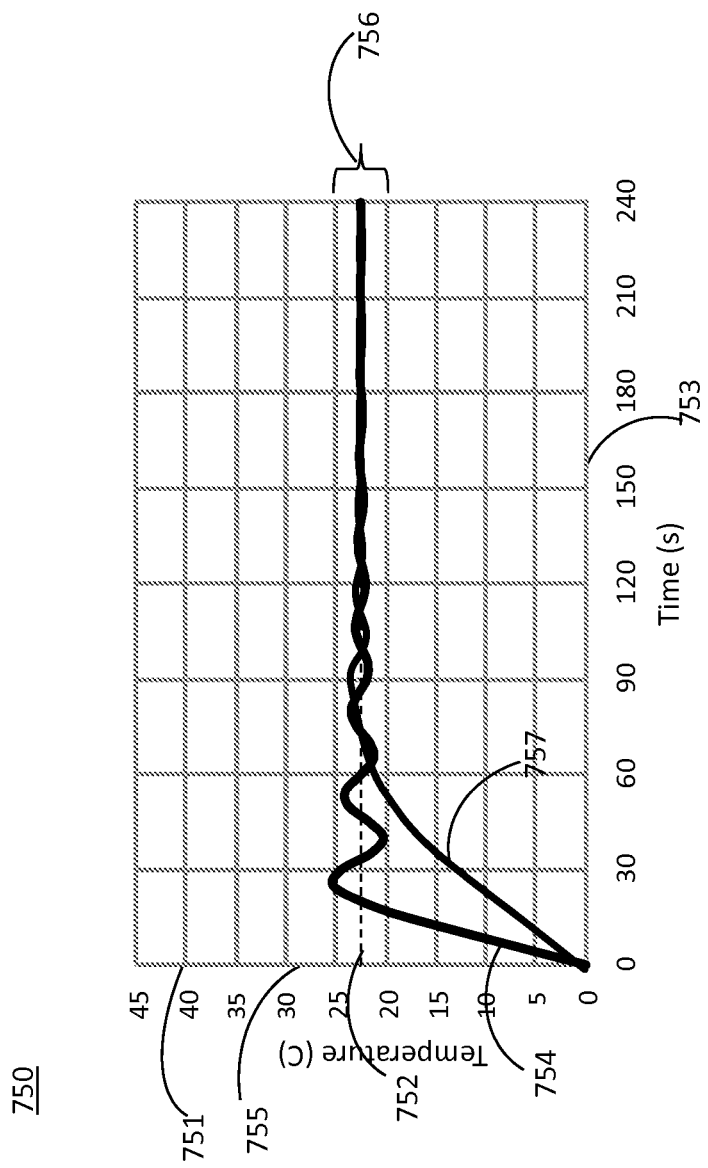
FIG. 7B is a graph showing various exemplary thermal profiles associated with an auto injector.

Moreover, details of an exemplary method associated with drug warming are provided with references to FIGS. 7A-7B. The method 700, for example, includes steps related to determination of whether a temperature of a drug is within a range of operating temperature values of the drug. The method also includes steps for adjusting the temperature of the drug to one of the operational temperature values, based on feedback from the heater temperature sensor 655 and the drug temperature sensor 660. The method further includes steps related to controlling the heater 650 to warm or adjust the temperature of the drug or drug cartridge 54.

Figure 10:
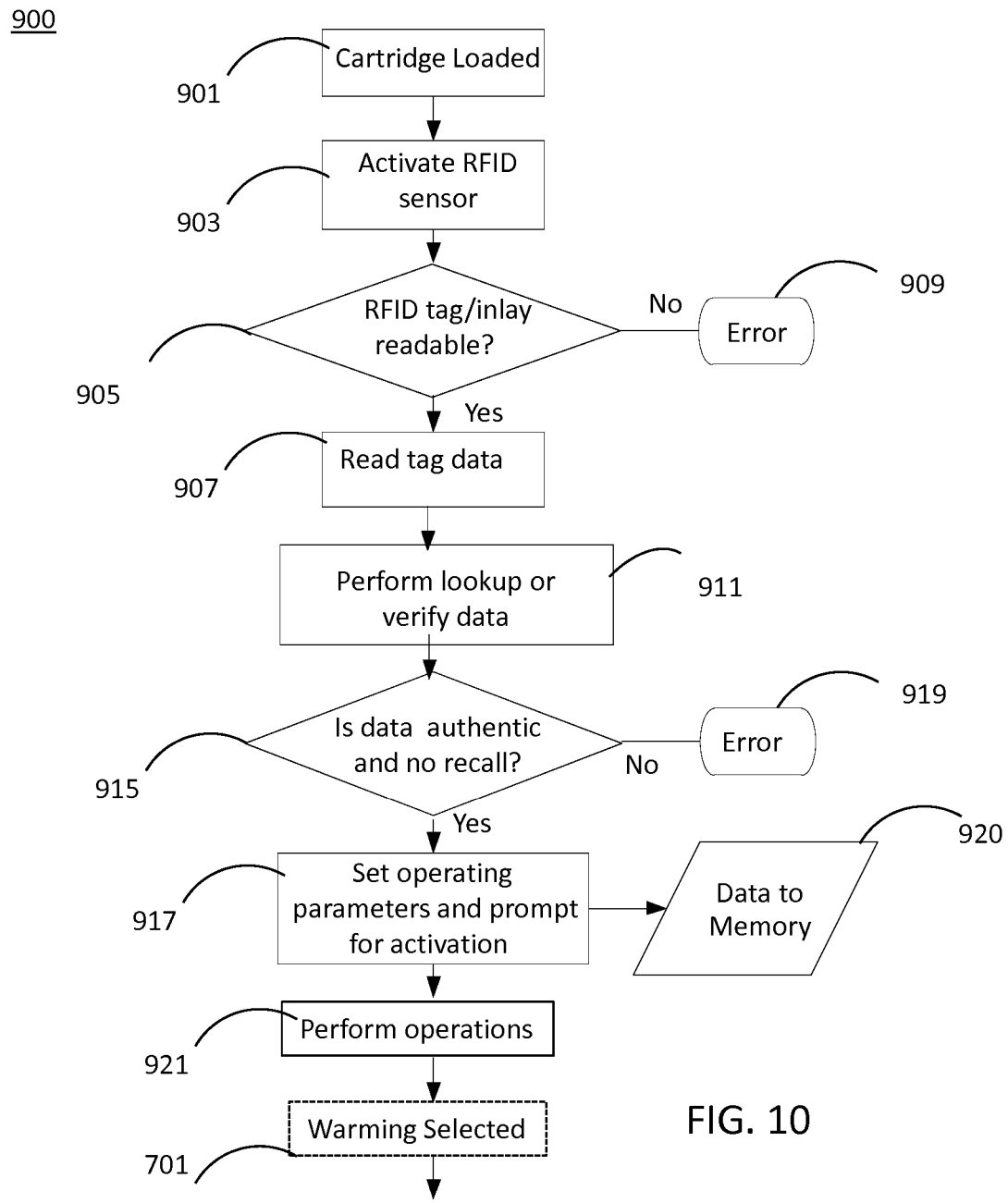
FIG. 10 is a flow chart illustrating an exemplary method for data communications between the RFID tag or inlay and the RFID antenna or sensor.

Referring now to FIGS. 7A and 10, the process flows depicted are merely embodiments of the invention and are not intended to limit the scope of the invention. For example, the steps recited in any of the method or process descriptions may be executed in any order and are not limited to the order presented. Furthermore, it will be appreciated that the following description makes appropriate references not only to the steps depicted in FIGS. 7A and 10, but also to the various system components as described with reference to the present invention.

As stated above, the drug profile and/or drug ID information may be obtained from the tag 820, via the RFID sensor 810 and/or the transceiver 830. Details about obtaining the data (e.g., drug profile) are now provided with reference to FIG. 10.

FIG. 10 is a flow chart illustrating an exemplary method 900 for data communications between the RFID tag or inlay 820 and the RFID antenna or sensor 810.

At step 901, a user may place the cartridge 54 within the cartridge carrier 126 which may cause the cartridge sensor 645 to send a signal to the main control unit 605 indicating the presence of the cartridge 54. Based on the received signal, the main control unit 605 may indicate that a cartridge 54 is loaded into the device 50. For example, the main control unit 605 may cause the display unit 645 to display appropriate message notifying the user of the loaded cartridge 54.

Completion of step 901 may cause automatic activation, or prompt the user to activate, certain operations of the auto injector 50. In at least one embodiment, the trigger of the cartridge sensor 645 (alone, after, or in combination with the cartridge cover sensor 615 signaling that the cartridge cover 72 is closed) may further trigger activation of a tag sensor 810 (as shown in step 903). For example, the tag sensor 605 may be powered up, and the main control unit 605 may cause the tag sensor 810 to emit radio frequency (RF) waves (e.g., an interrogating signal, as discussed above).

At step 905, the sensor 810 and/or the main control unit 605 may determine whether the tag 820 (on the loaded cartridge 54) is readable.

In one example, the sensor 810 may not receive a response signal from the cartridge tag 820 on cartridge 54 upon transmitting the interrogating signal. As such, at step 909, the sensor 810 and/or the main control unit 605 (e.g., via the signal received from the transceiver 830) may determine that the tag is not readable, or no tag is present on the cartridge.

Additionally, or alternatively, this step may further include an error check. For example, the sensor 810 may interrogate the tag 820 exclusively for a cartridge ID or a drug ID. If the tag 820 does not respond back (i.e., does not transmit any signal back to the sensor), the sensor 810 and/or the main control unit 605 may determine that the tag 820 is not readable. The method may then provide an error message to the user or prompt the user for further actions. For example, the auto injector 50 may prompt the user to replace the cartridge because it is not readable. The user may also be prompted to check whether the appropriate cartridge has been loaded in the device 50. This is may be an appropriate safety check as the device 50 may be configured for use with certain drug therapies or certain cartridges containing such therapies. Additionally or alternatively, the method may prompt the user to enter in necessary drug information and/or operational inputs through other means, as described elsewhere herein.

Alternatively, in some other embodiments, one or more parameters, or a combination of parameters from the cartridge tag may be used to determine whether the tag is readable.

The method 900 may determine that the tag 820 is readable based on the feedback received at step 905. In this example, the tag sensor 810 may receive a response signal (e.g., upon passing an error check) from the tag 820, upon transmitting the interrogating signal. At step 907, the tag sensor 810 may then retrieve and read the data, such as the drug profile from the tag 820.

As described herein, and shown in step 911, the data on the tag may be comprehensive of the drug profile and operational parameters that is verified by the device 50, or the tag 820 may contain exclusively a drug ID or other identification information, or any parameters, and/or a combination of parameters, that causes the device 50 to consult database or lookup tables stored in the storage units, or consult remote databases in order to obtain such information from external computer device.

In one example, the tag sensor 810 may retrieve the drug profile which may include, but not limited to, information related to drug identity, drug warming information, drug volume and drug viscosity, from the tag 820.

In another example, the tag sensor and/or the main control unit may only receive a drug ID from the tag 820. As such, the main control unit 605 may then consult internal and/or external storage units or computer devices to retrieve drug profile information that corresponds to the received drug ID or cartridge ID.

The main control unit 605 and/or sensor 810 may additionally decrypt or decode the data that is retrieved from the tag 820. Moreover, the main control unit and/or the sensor may verify that that data is not corrupted. For example, if it is determined that the retrieved data is corrupted at the first attempt, the sensor may repeat a predetermined number of times to retrieve the data from the tag 820. If the data cannot be retrieved after the predetermined number of attempts, the device 50 may notify the user and further request to check the cartridge.

The method 900 then proceeds to step 915. At step 915, the method may determine the authenticity of the retrieved data and/or to check if the drug is acceptable for use, and/or whether there has been a recall of the cartridge 54.

In one example, authenticity of the data and/or the acceptability of the use of the cartridge may be determined based on the manufacturer ID (i.e., the identity of the manufacturer who produced the drug), or any parameters, and/or a combination of parameters that may be included in the drug profile and/or any information received from the cartridge tag. The main control unit 605 may determine that there is a match (in one of the external or internal databases) to the received manufacturer ID. Based on the determination, the control unit may notify the user that the data received from the tag 820 is authentic. Additionally or alternatively, in another example, the main control unit may check the expiration date (which may be included in the drug profile) to determine whether there is a recall for the drug and/or whether the drug is acceptable for use.

If the data is not authenticated and/or there is a recall based on the manufacturing ID and/or the expiration date, in one example, the auto injector 50 may notify the user of an error, and prompt the user for action (step 919). It is noted that, this step may provide additional safety check by informing the user that the drug contained in the cartridge has been recalled and should be discarded, or that there is some other potential issue (e.g., the drug may not be from the original manufacturer, or the drug has expired). As such, in some examples, the cartridge or the drug product in the cartridge may be flagged as an unacceptable product.

The method may proceed to step 917 when it is determined (e.g., by the auto injector 50) that the data is authentic and that there is no recall for the drug, and/or the cartridge is acceptable for use. As such, the data or the drug profile received from the tag 820 may then be used to set the operating parameters of the device and/or prompt user for activation. In one example, data related to the operational temperature range of the drug, predetermined warming time, alarm temperatures, drug volume, drug viscosity, etc., may be received from the tag 820 via the tag sensor 810, based on which, the control unit may set the control loop parameters (e.g., PID parameters) to warm the drug to its operational temperature range within the predetermined time.

In another example, based on the received data (e.g., the drug volume and/or drug viscosity) from the tag sensor and tag 820, the control unit 605 may further retrieve a thermal profile (either from an internal or a remote storage device) that may be suitably used to warm the drug within a predetermined time.

Yet in another example, the control unit upon receiving the data of a drug from the tag sensor 820 may determine that the corresponding parameters and/or thermal profile are not up to date, and may then request a remote computer device (e.g., a server) for an update (e.g., via the communication unit) or download an update from the Internet. Additionally, or alternatively, the remote computer device may push an over-the-air (OTA) update (which may be related to the various parameters and/or a firmware update) to the auto injector 50, periodically (e.g., via the communication unit). Upon receiving the update, the auto injector may automatically install the data from the update. Alternatively, the auto injector may prompt the user of the availability of the update and may provide an option to selectively install the data from the update.

Moreover, it is contemplated that, the update may be location based. For example, when the user of the auto injector 50 arrives at a specific location (e.g., at a physician's office) and connects to a communication network or a computer device at that specific location, the auto injector may request for the update, and/or the update may be available upon arriving at the specific location.

At step 920, the operating parameters may be stored to the device memory (e.g., in an internal and/or an external storage unit), prior to, and/or after setting the parameters. These parameters may be reviewed by the user, healthcare provider, or a drug company, as discussed elsewhere herein, for example, to ensure that the drug was administered with the appropriate parameter settings.

The method 900 may then proceed to step 921 where the auto injector 50 may perform various operations, based on, for example, upon activation by the user. In one embodiment which incorporates a temperature sensing and temperature control element 520, step 701 may be performed as a first step of the flow chart described with reference to FIG. 7A. In some implementations, one or more operations at step 921 may be performed, prior to, during, or after step 701.

The auto injector 50 may be initialized for a drug delivery process when a user presses the activation button 501. In one example, the main control unit 605 may power up the auto injector 50 during the initialization of the auto injector 50 (e.g., at or before step 901). Upon receiving the activation signal, the main control unit 605 may optionally instruct the display unit 635 to display a welcome message.

Upon initialization, main control unit 605 may optionally communicate with various sensors and control units of the auto injector 50 to verify the operational status of the sensors and control units prior to, during or after the drug warming process. For example, if the main control unit 605 determines that one or more sensors are not fully operational, the main control unit 605 may provide the appropriate error messages to the user via the display unit 635. The main control unit 605 may optionally control various operations of the auto injector 50 prior to, during or after the drug warming process.

In one example, the main control unit 605 may optionally determine whether the energy source 108 has sufficient charge to complete a full drug delivery process including a warming process of the drug. The main control unit 605 may optionally consult the energy source sensor 620, or a control unit of the energy source 108 (not shown) to determine the charge capacity of the energy source 108. Based on the determination, the main control unit 605 may provide notifications via the display unit 635. For example, if the battery has enough charge for a complete drug delivery sequence, the auto injector device may prompt the user to continue with the current drug delivery process. Alternatively, if the battery or the energy source 108 does not have enough charge, the auto injector device may display a request message to charge the battery prior to initiation of the drug delivery process.

In one example, the user may optionally proceed to load or insert the cartridge 54 on the cartridge carrier 126 and subsequently close the cartridge cover 72 (e.g., when it is determined that there is sufficient change in the energy source 108). The main control unit 605, as discussed above, may consult with the cartridge sensor 645 to ensure that the cartridge 54 is correctly in position within the cartridge carrier 126 prior to the operation. This step may be optionally performed prior to, during, or after step 901.

In one implementation, the main control unit 605 may further consult with the timer unit 630 to determine whether a cartridge 54 is placed in the carrier 126 within a predetermined time. If the main control unit 605 does not receive a status signal from the cartridge sensor 645 within the predetermined time, the main control unit 605 may indicate a time-out and an appropriate error message may be displayed on the display unit 635. The user may also be prompted (on the display unit) to re-initialize the auto injector 50.

Additionally and/or alternatively, the main control unit 605 may identify that a cartridge (from a previous drug delivery sequence) is already present in the cartridge carrier, upon the initialization. As such, the user may be prompted to remove the old cartridge, in order to initiate a new drug delivery sequence with a new cartridge. This step may be optionally performed prior to, during, or after step 901.

Moreover, the main control unit 605 may consult the cartridge cover sensor 615 to ensure that the cartridge cover 72 is closed prior to the drug delivery process, and/or after the cartridge is properly placed in the carrier 126. If the main control unit 605, however, determines that the cartridge cover is not closed (upon consulting with the cartridge cover sensor), the main control unit may optionally send a request to the user (via a request message in the display unit) to close the cartridge cover in order to continue with the drug delivery process. This step may be optionally performed prior to, during, or after step 901.

Referring now to FIG. 7A, in one example, a user may be prompted by the auto injector 50 to warm a drug during a drug delivery process. For example, at step 701, upon inserting drug cartridge 54 containing the drug in the cartridge carrier 126, cartridge sensor 645 may be triggered that may cause (via the control unit 605) an option for warming the drug to be displayed on display unit 635. The user may respond to the prompt by selecting (e.g., by pressing activation button or by providing touch input on the display screen) the warming option of the drug. In another example, the user may skip the warming of the drug by not selecting the drug warming option. Alternatively, the user may press the activation button a pre-determined number of times to select the warming option after inserting the drug cartridge 54 (e.g., when a display option is not provided).

It is contemplated that a user may program the auto-injector 50 to provide or not provide the drug warming option, each time the user initiates operation of the auto injector 50 for a drug delivery process.

Additionally, as discussed above, the auto injector 50 may optionally determine the identity of the drug based on the syringe tag 820 provided on the cartridge 54. Auto injector 50 may utilize an RFID sensor 810 to recognize the drug based on the syringe tag 820 or drug ID. For example, the control unit 605 may match the decoded drug ID retrieved or received from the syringe tag 820 with one of the stored drug IDs (stored in a lookup table and/or in a database of the storage unit 640). Alternatively, the auto injector may communicate with a cloud based storage system in order to access the appropriate drug ID. Once, the control unit determines there is a match, the control unit 605 may then associate the identified drug with a drug profile information of the drug (e.g., information related to the operating temperature of the drug, time within which the drug need to be warmed, viscosity of the drug, volume of the drug, etc.). The association may be based on accessing the drug profile from the storage unit 640 or from a cloud based storage.

Yet in another embodiment, the user may indicate an identity of a drug by pressing the activation button a predetermined number of times (e.g., pressing the activation button 4 times may indicate drug A) or by interacting with the display unit, and based on the indication, the main control unit 605 may retrieve the drug profile of the drug and other appropriate information related to the drug.

Upon the selection of the warming option of the drug, at step 703, the main control unit 605 may power up the heater 650 of the auto injector 50. Moreover, a notification may optionally be displayed on the display unit 635 (e.g., heater ON) to indicate the operational status of the heater 650.

At step 705, the main control unit 605 may receive inputs or feedback from the heater temperature sensor 655 and the drug temperature sensor 660. For example, the heater temperature sensor 655 may detect and send temperature information of the heater to the main control unit 605, and the drug temperature sensor 660 may detect and send temperature information of the drug to the main control unit 605.

At step 707, when the temperature sensors 655 and 660 detect that the temperatures of the heater 650 and temperature of the drug are above an alarm point temperature or below another alarm point temperature value, the main control unit 605 may determine that the drug warming operation may not be operated. As such, the main control unit 605 may then cause the display unit 635 to display an error notification (step 709). The alarm point temperatures may be stored locally in the storage units (not shown) of the respective sensors 655 and 660. In one example, the storage units may be electrically erasable programmable read only memory (EEPROM) units that may be programmed by an administrator with the alarm point temperature values during a manufacturing process.

In one example, an alarm point temperature value may be 40° C. (see 751 in FIG. 7B). In another example, an alarm point temperature may be 5° C. As such, when the temperature sensors 655 and 660 detect any temperature of the heater and/or the drug to be at or above 40° C., or at or below 5° C., alarm pins (not shown) in the respective temperature sensors may be triggered, causing the main control unit 605 to proceed to step 709. In one example, the main control unit 605 may power down the auto injector 50 at step 709, if the detected temperatures remain above or below the alarm point temperatures for a predetermined time (e.g., 2 minutes), for safety reasons.

At step 707, the main control unit 605 may determine that the detected temperature of the heater 650 and the drug or drug cartridge 54, are not above the alarm point temperature (e.g., the detected temperatures are not above 40° C.) or below the alarm point temperature (e.g., the detected temperatures are not below 5° C.) based on the feedback received from the heater temperature sensor 655 and drug temperature sensor 660, respectively. Additionally, the main control unit 605 may further determine that the detected temperature of the drug is below 20° C. (e.g., 18° C.). The main control unit may then consult the drug profile of the drug. In one example, the drug profile may indicate that the operating temperature of the drug is 22.5° C., and the range of the operating temperature values is +/−2.5 C (see 752 and 756 of FIG. 7B). That is, the range of operating temperature values of the drug is between 20° C. and 25° C. As such, the main control unit 605 may determine that the current drug temperature (i.e., 18° C.) is below the operating temperature of the drug (i.e., 22.5° C.). Additionally, the main control unit may further determine that the predetermined warming time of the drug is at least 4 minutes (based on the stored drug profile of the drug). The determination performed by the control unit 605, may be based on the retrieved data from the tag that is received via the tag sensor 810 (e.g., via the transceiver 830).

At step 711, the main control unit (upon being programmed as a PID controller, as discussed above) may send command signals (e.g., modulated voltage signals) to the heater 650 to warm the drug. As shown in FIG. 7B, in one example, a thermal profile of the drug may follow the curve 754.

At step 713, the main control unit 605 may receive temperature feedback from the drug temperature sensor 660. Based on the feedback, the main control unit may adjust the temperature of the drug to bring the temperature to the range of operating temperature values of the drug (e.g., 756 of FIG. 7B). Adjustment may include, sending command signals, by the main control unit 605, to the heater 650 to raise or not raise the temperature. For example, a switch (not shown) may be implemented by the control unit 605 to switch off and on the current flow to the heater 650. Moreover, the heater temperature sensor 655 may continue to detect the temperature of the heater 650 and send feedback to the main control unit 605. Based on the feedback, the main control unit 605 may determine that no alarm point has been triggered.

In this way, the main control unit 605 may continue the adjustment process until the temperature detected by the drug temperature sensor 660 reaches the operating temperature (e.g., 752) or lies within the operating temperature range 756 of the drug within the predetermined time (e.g., within 240 seconds).

As mentioned above, in some implementations, the adjustment process performed by the PID control/control unit 605 may be based on the retrieved data/and or drug profile from the tag sensor that is received via the tag sensor 810 and stored in the storage unit 640, and/or optionally based on parameters set at step 917.

At step 715, when the main control unit 605 determines based on the temperature feedbacks, the detected temperature of the drug is not within the range of the operating temperature values (e.g., 756), the main control unit 605 loops back to step 711.

In one example, when the main control unit 605 determines that the temperature of the drug has reached the operating temperature value, the method then proceeds to step 719.

A discussion is now provided of the thermal profiles of the drug with reference to FIG. 7B. As shown in FIG. 7B, curve 754 shows an exemplary thermal profile of the drug. The thermal profile indicates the variation of the drug temperature 755 with respect to time 753 when the main control unit controls the feedback loop during the warming operation of the drug.

It is noted that, upon accessing the drug profile (e.g., drug viscosity information, drug volume information, operating temperature values, predetermined warming time of the drug, drug expiration date, etc.,) of the drug, the main control unit 605 may determine how the drug would be warmed. Moreover, the main control 605, based on the determination, may adjust and modify the parameters of the control loop to cause the warming of the drug (that may follow one of the thermal profiles). Graph 750 shows exemplary thermal profiles 754, 757. For example, based on the accessed drug information, the main control unit 605 may determine that the temperature of the drug may need to be increased rapidly and then allow oscillation, prior to reaching the operating temperature within a predetermined time. In such a case, the warming of the drug may follow the thermal profile 754. In another example, the main control unit 605 may determine that the temperature of the drug may need to be ramped up slowly or gradually prior to reaching the operating temperature of the drug. In such a case, the warming of the drug may follow the thermal profile 757. It is noted that, thermal profile 757 may be a thermal profile of the same drug or a different drug, and the temperature of operation for the drug could be any value within the region of 756. The thermal profile may be based on one or more of: drug requirements, power optimization, minimization of heating duration, and parameters set at step 917

Referring back to FIG. 7A, at step 719, the main control unit 605 may determine that the operating temperature of the drug has been achieved, and the main control unit may then store information of the operating temperature (i.e., the actual operating temperature that was reached upon warming) and the time that was required to reach the operating temperature (i.e., the warming time of the drug) along with any other appropriate information related to the warming of the drug.

At step 720, the main control unit may transfer this data to the storage unit 640. In one example, the data may be later accessed and processed by physicians of the user. The data may be transferred to another device (e.g., a mobile user device) via communication unit 680. Alternatively, or additionally the data may be stored in an external storage device. The data may be reviewed by the user, healthcare provider, or a drug company, as discussed elsewhere herein, for example, to ensure that the drug was administered with the appropriate parameter settings.

At step 721, upon the completion of the drug warming process, the main control unit 605 may optionally cause the display unit 635 to display a notification to indicate that the drug warming process has been completed.

It is noted that, in some examples, the auto injector 50 may not be able to warm the drug properly, for example, due to malfunctions of the heater 650 or temperature sensors, or due to overshooting the predetermined warming time. In such cases, the auto injector 50 may provide appropriate notifications (related to the malfunctions or error) to the user via the display unit 635 and/or audible tones. Additionally or alternatively, the auto injector 50 may be programmed to notify the user of alternate ways to warm the drug or entirely skip the warming process.

The main control unit 605, upon completion of the drug warming process 700, may optionally prompt the user to remove the needle shield 60 and/or be notified that needle shield removal will commence. Once the user removes the needle shield 60, the main control unit 605, may then further prompt the user to initiate the drug delivery sequence (e.g., by pressing the activation button 501).

It is noted that, once the needle shield is removed, the cartridge needs to be used for an injection (i.e., for the drug delivery dose). If the auto injector is powered off before the dose is delivered, cartridge 54 may not be used by the auto injector 50. Accordingly, the main control unit 605 may provide the appropriate notification (e.g., via the display unit) to the user and a new cartridge may need to be warmed again prior to the drug delivery process. Additionally, if the needle shield has been removed, the control unit may prevent the opening of cartridge cover 72 until the needle shield has been replaced or needle retraction has occurred.

Moreover, once the drug delivery sequence is initiated, in order to open the cartridge cover and remove the cartridge 54, the user may need to cancel the injection. If the user cancels the current injection, the door open option will appear (e.g., on the display unit) and the user may then remove the cartridge from the device.

Additionally, after the drug warming process has been completed, the user may be optionally prompted on the display unit 635 to hold the auto injector 50 against the injection site. For example, the main control unit 605 may instruct the display unit to display an appropriate notification for holding the auto injector 50 against the injection site. Once the user places the auto injector 50 against the injection site, the main control unit 605 may determine whether a skin portion of the user is substantially proximate or in contact with the auto injector 50 (based on feedback received from a skin sensor of the auto injector (not shown)). Once the skin contact is established, and the dose sequence has been initiated, the auto injector device enters into the drug delivery phase.

It is noted that, if the user wishes to cancel the injection after the needle shield removal (and after initiating the dosing sequence), the dose must be expended or wasted before the cartridge is removed from the auto injector. Similarly, if the complete dose is not delivered, the user must waste the remaining dose before opening the cover and removing the cartridge 54 from the auto injector. For example, the main control unit 605 may receive a signal for cancellation (e.g., user may press the activation button 501 a predetermined number of times to indicate cancellation) of the drug delivery. The main control unit 605 may then prompt the user to expend the drug that is inside the cartridge. For example, the main control unit 605 may provide instruction such as to go near a waste basket to expend the remaining drug inside the cartridge.

Once the drug has been delivered, the user may be prompted of an end of dose notification. The main control unit 605 may optionally further prompt the user to remove the cartridge 54 after the end of dose notification. In one example, the main control unit 605 may not allow the user to shut down the auto injector 50 until the used cartridge 54 has been removed from the auto injector 50.

As discussed above, one or more sensors may be utilized for safety of the auto injectors. For example, temperature sensors 655 and 660 may be utilized to ensure that a drug is warmed to its operating temperature prior to the drug delivery. Cartridge sensor 645 may similarly be used to ensure that a cartridge 54 is correctly in position within the cartridge carrier 126 prior to an operation. Other sensors known in the art may be utilized for this or other purposes and are contemplated and encompassed within the breadth of the embodiments of the present invention. Similarly, other components may optionally be utilized to enhance the safety and functionality of the automatic injector 50. For example, a cartridge ejector assembly 182 may be utilized to removably lock and eject the cartridge 54 during and after an operation, respectively. One example of a cartridge ejector assembly 182 is shown in FIG. and 4. Cartridge ejector assembly 182 may be controlled by the main control unit 605 upon being coupled to the drive unit 610.

Moreover, if a safety syringe is utilized as a cartridge 54 of the automatic injector 50, safety mechanisms of the safety syringe may be triggered at the end of the drug delivery stage by operation of the syringe. In this case, drive unit 610, for example, may indicate the end of the drug delivery stage to the main control unit 605. Accordingly, the cartridge 54 disposed in the cartridge carrier 126 of the automatic injector 50 will be safe for removal and disposal by the user. Optionally, the user may reattach the rigid needle shield 60 to the distal end of the cartridge 54, such as to the distal end of the barrel 56, after the syringe has been used.

The reusable automatic injectors 50 of the present invention are able to accommodate partially or fully filled cartridges 54 of varying capacity, including 1 mL cartridges 54. The reusable automatic injector could be used with retractable or safety syringes, including prefilled syringes, as well as with non-safety syringes. When used with a non-safety syringe, the cartridge 54 is fully withdrawn back into the reusable automatic injector housing 52 after the injection or upon loss of contact with the patient's skin to protect the user from exposed needles. Following the injection complete signal or upon retraction of the cartridge, the user can re-cap the non-safety syringe whilst it remains in the reusable automatic injector housing 52 with no risk of a needlestick injury as the needle point is contained inside the housing 52. The reusable automatic injector or cartridge cover 72 can then be opened and the used cartridge 54 can be safely disposed in a sharps container. The reusable automatic injector 50 would therefore provide a safe injection for non-safety syringes in addition to working with most retractable needle syringes. The present invention also provides reusable auto injectors which are ergonomic, easy-to-use and aesthetically similar to products currently employed by self-administering patients. The automatic injectors of the present invention provide sufficient force at suitable speeds to simulate an injection by a nurse or doctor, yet provide the freedom of use for self-administering patients. The reusable automatic injectors of the present invention are also configured to withstand frequent use, such as daily use, over an extended period of time. The energy source which powers the reusable automatic injectors may similarly be replaceable, rechargeable, or otherwise provide power for use of the injectors over an extended period of time. The present invention thereby provides a reusable automatic injector with integrated safety mechanisms, enabled by incorporating a retractable needle syringe within the reusable automatic injector, in a convenient and easy-to-use package for patients.

The present invention provides a method that includes: detecting, a first temperature value of a heater, by a first sensor that is positioned in close proximity to the heater, and wherein the heater is positioned in close proximity to a cartridge adaptively containing a drug. The method detects a second temperature value of the drug, by a second temperature sensor that is positioned in close proximity to the drug. The method further determines, whether the detected first temperature of the heater is below a first alarm set point temperature value and the detected second temperature value of the drug is within a range of drug operating temperature values, by a feedback control unit that is electrically coupled to the heater, the first temperature sensor and the second temperature sensor. The method includes a step of adjusting, by the feedback control unit, the detected second temperature value of the drug to an operational temperature value of the drug that is within the range of drug operating temperature values based on the determination that the first detected temperature value is below the first alarm set point temperature value and the detected second temperature value is not within the range of drug operating temperature values.

One or more of the embodiments described above may provide additional desirable features to the patient. For example, the automatic injectors or the control system 600 of the present invention may utilize existing or additional components within the housing to limit the depth of needle insertion. In one such embodiment, features located on the housing or the guide may be utilized for this purpose. In another embodiment, mechanical limits may be integrated into the drive unit (e.g., drive control mechanism, the cartridge carrier, the plunger carrier, or the drive screw) to limit the range of travel of the syringe needle into the patient. Similarly, as described above, one or more components may be employed to automatically remove the needle shield from the syringe needle upon activation of the reusable auto injector.

In another embodiment, a single automatic injector according to the invention may be adjusted to accommodate cartridges including needles of various lengths. In this way, a single automatic injector may be utilized, for example, for intramuscular injections and subcutaneous injections. In adjusting for various needle lengths, the automatic injector may include a mechanical adjustment and/or an electrical adjustment, for example, by way of the user interface. The depth of needle insertion may be adjusted based upon the movement of the cartridge carrier within the housing.

The embodiments shown and detailed herein disclose only a few possible variations of the present invention; other similar variations are contemplated and incorporated within the breadth of this disclosure. As would be readily appreciated by an ordinarily skilled artisan, a number of parameters, shapes, and dimensions described above may be modified while remaining within the breadth and scope of the present invention. Such automatic injectors may be employed by, for example, patients who are required to self-inject their medication on a regular or long-term basis. Accordingly, similar to the examples provided above, the auto injectors of the present invention may be configured, modified, and utilized to initiate drug delivery and activate needle retraction in any number of configurations while remaining within the breadth and scope of the present invention. Thus, it is intended that the present invention covers the modifications and variations of this invention provided they come within the scope of the appended claims and their equivalents.

It will be appreciated that the foregoing description provides examples of the disclosed system and technique. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context.

Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

What is claimed is:

1. A drug delivery device configured to sense and control temperature of a cartridge containing a drug, the drug delivery device comprising:
    a housing;
    a cartridge carrier configured to receive at least a portion of the cartridge;
    a plunger carrier disposed for movement relative to the cartridge carrier and configured to engage a plunger assembly of the cartridge;
    a drive control mechanism coupled to the plunger carrier and configured to control movement of the plunger assembly; and
    a temperature control system comprising:
        a heater that is configured to be in close proximity to the cartridge and configured to warm the drug;
        a first temperature sensor that is positioned in close proximity to the heater and configured to detect a first temperature value of the heater;
        a second temperature sensor that is positioned in close proximity to the cartridge and configured to detect a second temperature value of the drug; and
        a control unit that is electrically coupled to the heater, the first temperature sensor and the second temperature sensor; and the control unit being configured to:
            determine whether the detected first temperature value of the heater is below a first alarm set point temperature value and the detected second temperature value of the drug is within a range of drug operating temperature values; and
            restrict operation of the drive control mechanism and adjust the detected second temperature value of the drug to an operational temperature value of the drug that is within the range of drug operating temperature values if it is determined that the first detected first temperature value is below the first alarm set point temperature value and the detected second temperature value is not within the range of drug operating temperature values.

2. The drug delivery device of claim 1, wherein the control unit is a feedback control unit that receives the detected first and the second temperature values from the first and the second temperature sensors, respectively.

3. The drug delivery device of claim 1, wherein the control unit transmits an error signal upon determination that the detected first temperature value of the heater is above the first alarm set point temperature value or below a second alarm set point temperature value.

4. The drug delivery device of claim 3, wherein the first alarm set point temperature value and the second alarm set point temperature values are pre-determined values that are programmed in a storage unit associated with the first temperature sensor.

5. The drug delivery device of claim 1, wherein the adjustment of the detected second temperature value further includes transmission of a command signal, by the control unit, to the heater to warm the drug within a predetermined time while monitoring the first temperature value of the heater.

6. The drug delivery device of claim 5, wherein the control unit controls the transmitted command signal to warm the drug via the heater within the predetermined time based on a thermal profile of the drug.

7. The drug delivery device of claim 1, wherein the control unit transmits an error signal to a display unit that is coupled to the control unit upon determining that the second temperature was not adjusted to the operational temperature value within a predetermined time.

8. The drug delivery device of claim 1, wherein the control unit prompts a user to activate one or more operations related to drug delivery from the cartridge upon the adjustment of the second detected temperature to the operational temperature value.

9. The drug delivery device of claim 1, wherein the control unit further stores the operational temperature value, after the adjustment of the detected second temperature of the drug, in a storage unit that is coupled to the control unit.

10. The drug delivery device of claim 1, wherein the range of drug operating temperature values has an upper limit value and a lower limit value that are programmed to be percentages of a desired operating temperature of the drug.

11. The drug delivery device of claim 1, wherein the control unit transmits a command signal to the heater upon receiving an activation signal from a user that indicates initiation of warming of the cartridge containing the drug.

12. The drug delivery device of claim 1 further comprising an identification system configured to identify the cartridge containing the drug, the identification system comprising:
a tag sensor that is electrically coupled to the control unit, wherein the control unit activates the tag sensor to initiate a contactless communication with the cartridge upon detecting a presence of the cartridge.

13. The drug delivery device of claim 12, wherein the control unit transmits a command signal to the heater upon receiving an activation signal from the tag sensor that indicates that the tag sensor is activated and has wirelessly received drug information from a cartridge tag.

14. The drug delivery device of claim 12, wherein the adjustment of the detected second temperature further includes transmission of a command signal to the heater to warm the drug within a predetermined time based on warming period information received from a cartridge tag.

15. The drug delivery device of claim 12 further comprising a communication unit, wherein the control unit stores the operational temperature value after the adjustment of the detected second temperature of the drug in a remote storage unit via the communication unit.

16. The drug delivery device of claim 12, wherein the control unit controls the cartridge carrier to move the cartridge from a first position where a needle of the cartridge is within the housing, to a second position where the needle extends distally from the housing, based on the information received from at least one of the temperature control system and the identification system.

17. The drug delivery device of claim 12, wherein the control unit comprises a first control unit associated with the temperature control system and a second control unit associated with the identification system.

18. The drug delivery device of claim 12 further comprising a sensor carriage configured to receive the tag sensor, wherein the control unit activates the tag sensor to initiate a contactless communication with the cartridge upon detecting the presence of the cartridge within the sensor carriage.

19. The drug delivery device of claim 12, wherein motion of the plunger carrier is controlled by the control unit based on the information received by the tag sensor from a cartridge tag to control a rate of drug delivery.

20. The drug delivery device of claim 1, wherein the control unit is further configured to control the drive control mechanism to deliver the drug upon determination of the detected second temperature value of the drug being at the operational temperature value.

21. The drug delivery device of claim 1, wherein the heater and the first and second temperature sensors are disposed on the cartridge carrier.

* * * * *